(12) United States Patent
Kobayashi

(10) Patent No.: US 6,491,628 B1
(45) Date of Patent: Dec. 10, 2002

(54) ELECTRONIC ENDOSCOPE

(75) Inventor: Hiroyuki Kobayashi, Tokyo (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/865,708

(22) Filed: May 29, 2001

(30) Foreign Application Priority Data

May 31, 2000 (JP) ........................................ 2000-161773

(51) Int. Cl.[7] ................................................. A61B 1/00
(52) U.S. Cl. ........................................ 600/168; 348/65
(58) Field of Search ................................ 600/168, 109, 600/160; 348/65, 220, 221, 240

(56) References Cited

U.S. PATENT DOCUMENTS

| | | |
|---|---|---|
| 5,871,439 A | 2/1999 | Takahashi et al. |
| 5,929,900 A * | 7/1999 | Yamanaka et al. ........... 348/220 |
| 6,078,353 A * | 6/2000 | Yamanaka et al. ............ 348/65 |
| 6,117,071 A | 9/2000 | Ito et al. |
| 6,322,497 B1 * | 11/2001 | Takahashi .................... 348/65 |

* cited by examiner

Primary Examiner—John Mulcahy
(74) Attorney, Agent, or Firm—Greenblum & Bernstein, P.L.C.

(57) ABSTRACT

An electronic endoscope having a video-scope with an image sensor, a video-processor and a display has an image forming processor, a signal processor and a display-state changing processor. The signal processor generates video signals on the basis of image-pixel signals from the image sensor and outputs said video signals to said display. The display-state changing processor changes a display-state from a normal-display to a magnified-display and from the magnified-display to the normal-display. In the case of the normal-display, the image forming processor forms a normal-display subject image composed of a smaller number of pixels than that of the all-pixel subject image. In the case of the magnified-display, the image forming processor forms a magnified-display subject image composed of pixels arranged within a part-area.

16 Claims, 14 Drawing Sheets

ELECTRONIC ENDOSCOPE

BACKGROUND OF THE INVENTION

1. Field of the Invention

The present invention relates to an electronic endoscope having a video-scope with an image sensor and a video-processor. In particular, this invention relates to a magnified-display, which magnifies a portion of an observed image displayed on the monitor.

2. Description of the Related Art

Recently, a magnifying electronic endoscope was provided, which is capable of magnifying a specific portion of an observed image displayed on a monitor and displaying a magnified image. The magnifying electronic endoscope has an optical magnifying function, or an electric magnifying function.

The optical type endoscope has a zoom lens movable along the optical axis. The specific portion of the displayed image is magnified by driving the zoom lens so that the magnified specific portion image is displayed on the monitor. In the optical magnifying method, picture quality does not degrade. However, when the image is optically magnified, the visual field becomes narrow and the depth of focus is reduced, in other words, the focusing range becomes narrow. Therefore, to continue capturing the specific portion in the visual field is difficult because a hand tremble, caused by the operator holding the video-scope, or the movement (tremble) of the organ itself affects the image.

On the other hand, the electric magnifying method securely captures the specific portion as the depth of focus is not changed. However, as a process, which interpolates pixels, is performed to the original displayed image, the picture quality degrades, so that the magnified specific portion cannot be precisely diagnosed.

SUMMARY OF THE INVENTION

Therefore, an object of the present invention is to provide an electronic endoscope that electrically magnifies a specific portion of an original image without degrading the picture quality.

An electronic endoscope of the present invention is provided that consists of a video-scope with an image sensor, a video-processor and a display. The video-scope for capturing an observed-subject is detachably connected to the video-processor and the display is connected to the video-processor. The electronic endoscope has an image forming processor, a signal processor and a display-state changing processor. Based on an all-pixel subject image, which is formed on the image sensor and composed of substantially all pixels in the image sensor, the image forming processor forms a display subject image to be displayed on a monitor. The display subject image is formed in accordance with a video standard (video scanning standard), upon which resolution of the display depends. For example, a color television standard, such as the NTSC method, the PAL method, or a computer video standard, such as the VGA standard, SVGA standard, is applied. The signal processor generates video signals or the basis of image-pixel signals corresponding to the display subject image and outputs the video signals to the display, so that an observed image, corresponding to the observed image formed by the image forming processor, is displayed.

The electronic endoscope of the present invention has a function for magnifying a specific portion of the displayed observed image. The display-state changing processor changes the display-state from a normal-display to a magnified-display and from the magnified-display to the normal-display. In the normal-display, the image forming processor forms a normal-display subject image, composed of a smaller number of pixels than that of the all-pixel subject image, as the display subject image. Image-resolution, or image-size, of the normal-display subject image is different from that of the all-pixel subject image. In the magnified-display, the image forming processor forms a magnified-display subject image composed of pixels arranged within apart-area of the all-pixel subject image as the display subject image, so that a magnified-image is displayed. When the electronic magnifying process is performed, the magnified-image is obtained without performing the interpolation process, which results in a degradation of picture quality. Therefore, a diseased portion is precisely diagnosed. Preferably, the image forming processor forms the normal-display subject image by performing a down sampling to the all-pixel subject image.

To obtain high picture quality normal-display subject image and magnified-display subject image respectively, preferably, the pixel number of the image sensor is larger than an effective pixel number that corresponds to the applied video standard. Note, the effective pixel number exhibits the resolution of the display. Namely, the effective pixel number represents the number of pixels that can be used for an image. For example, in the NTSC method, the effective pixel number is approximately 410,000 and an image sensor having pixels more than one million pixels can be advantageously used. The normal-display subject image and the magnified-display subject image are composed of a first pixel number and a second pixel number respectively, both of which are equal to and less than the effective pixel number. The image forming processor may compose the normal-display and magnified-display subject images with a number of pixels near to the respective effective pixel numbers, so that high picture-quality images are obtained in both the normal-display and the magnified-display.

The pixel number of the image sensor used at the electronic endoscope varies with the type, or manufacturing time of the video-scope. Therefore, preferably, the electronic endoscope further has a pixel number determining processor that determines whether or not the pixel number of the image sensor is larger than the effective pixel number. When the pixel number is larger than the effective pixel number, the image forming processor forms the normal-display subject image and the magnified-display subject image. On the other hand, when the pixel number of the image sensor is not larger than the effective pixel number, the image forming processor forms the all-pixel subject image as the normal-display subject image during the normal-display and forms the magnified-display subject image by performing an interpolation process to the all-pixel subject image during the magnified-display. As down sampling is not performed in the normal-display when the pixel number is small, the resolution of the observed image in the normal-display does not degrade.

Preferably, the electronic endoscope has an input device so that the operator can select a portion to be magnified from the observed image displayed at the normal-display. The input device is operated to indicate a given position in the normal-image, corresponding to the normal-display subject image. When using the input device, the electronic endoscope has an indicating pixel detecting processor. The detecting processor detects an indicated-position set by the input device and specifies an indicating-pixel corresponding to the indicated-position from the pixels of the all-pixel subject image. The image forming processor forms the magnified-display subject image by defining the indicating-pixel as a center pixel of the part-area and defining the part-area composed of the second pixel number.

For example, the input device is a keyboard, which has been used as an input device for the electronic endoscope. In this case, the electronic endoscope has an indicator mark displaying processor, that generates a character signal corresponding to an indicator mark, and superimposes the character signal upon the video signals such that the indicator mark indicates the given position. The keyboard is connected to the video-processor and has shift keys for shifting a position of the indicator mark on the display. The indicator mark displaying processor adjusts the position of the indicator mark in accordance with the operation of the shift keys. Then, the indicating pixel detecting processor detects the position of the indicator mark as the indicated-position and specifies the indicating-pixel from the position of the indicator mark.

On the other hand, a touch panel may be used for the input device. The touch panel is connected to the video-processor and arranged on the display. The touch panel identifies a position touched by an operator and informs the video-processor. The indicating pixel detecting processor detects the touched position as the indicated-position and specifies the indicating-pixel accordingly.

Preferably, the indicating pixel detecting processor determines whether or not the part-area composed of the second pixel number can be defined in the all-pixel subject image on the condition that the indicating-pixel becomes the center position of the magnified-display subject image. When the part-area cannot be defined, the indicating pixel detecting processor changes the indicating-pixel position such that a magnified-display subject image composed of the second pixel number is formed. The magnified-display subject image is usually composed of the second pixel number.

Preferably, the image forming processor forms the display subject image in the video-scope. In this case, a video-processor is obtained by a minimum modification to the structure of the conventional video-processor. Preferably, the image forming processor forms the normal-display subject image by performing a down sampling. The down sampling reads only image-pixel signals, generated in pixels, by which the normal-display subject image is formed, from the image sensor. Further, the image forming processor forms the magnified-display subject image by reading only image-pixel signals, generated at the pixels arranged within the part-area, from the image sensor. Thus, the structure for forming the display subject image at the video-scope is simplified.

Preferably, a manipulating member for shifting the position of the indicator mark is attached at a manipulating section of the video-scope. The indicator mark displaying processor adjusts the position of the indicator mark in accordance with an operation of the manipulating member. The indicating pixel detecting processor detects the position of the indicator mark as the indicated-position and specifies the indicating-pixel from the position of the indicator mark. The operator may shift the indicator mark with manipulating the video-scope. To make the manipulation easy, preferably, the manipulating member has a plurality of push buttons for shifting the indicator mark, the indicator mark displaying processor adjusting the position of the indicator mark in accordance with the operation of the plurality of push buttons. For example, the manipulating member is composed of first, second and third push buttons arranged on a tapering end portion of the manipulating section, the first push button arranged on one surface of the tapering end portion and the second and third push buttons arranged on another surface of the tapering end portion. The first, second and third push buttons are arranged such that at least two buttons of the first, second and third push buttons can be operated simultaneously by at least two fingers of thumb, index and middle fingers.

According to another aspect of the present invention, an apparatus for displaying normal and magnified images is incorporated in an electronic endoscope having a video-scope with an image sensor, a video-processor and a display. The video-scope and the display are connected to the video-processor. The apparatus has an image forming processor, a signal processor and a display-state changing processor. The image forming processor forms a display subject image on the basis of an all-pixel subject image, as formed on the image sensor, and substantially composed of all of the pixels in the image sensor. The signal processor generates video signals on the basis of image-pixel signals corresponding to the display subject image and outputs the video signals to the display. The display-state changing processor changes the display-state from a normal-display to a magnified-display and from the magnified-display to the normal-display. The image forming processor forms a normal-display subject image composed of a smaller number of pixels than that of the all-pixel subject image, as the display subject image, during the normal-display. Image-resolution of the normal-display subject image is different from that of the all-pixel subject image. Further, the image forming processor forms a magnified-display subject image composed of pixels arranged within a part-area of the all-pixel subject image as the display subject image during the magnified-display.

BRIEF DESCRIPTION OF THE DRAWINGS

The present invention will be better understood from the description of the preferred embodiment of the invention set forth below together with the accompanying drawings, in which.

DESCRIPTION OF THE PREFERRED EMBODIMENTS

Hereinafter, the preferred embodiment of the present invention is described with reference to the attached drawings.

Figure 1:
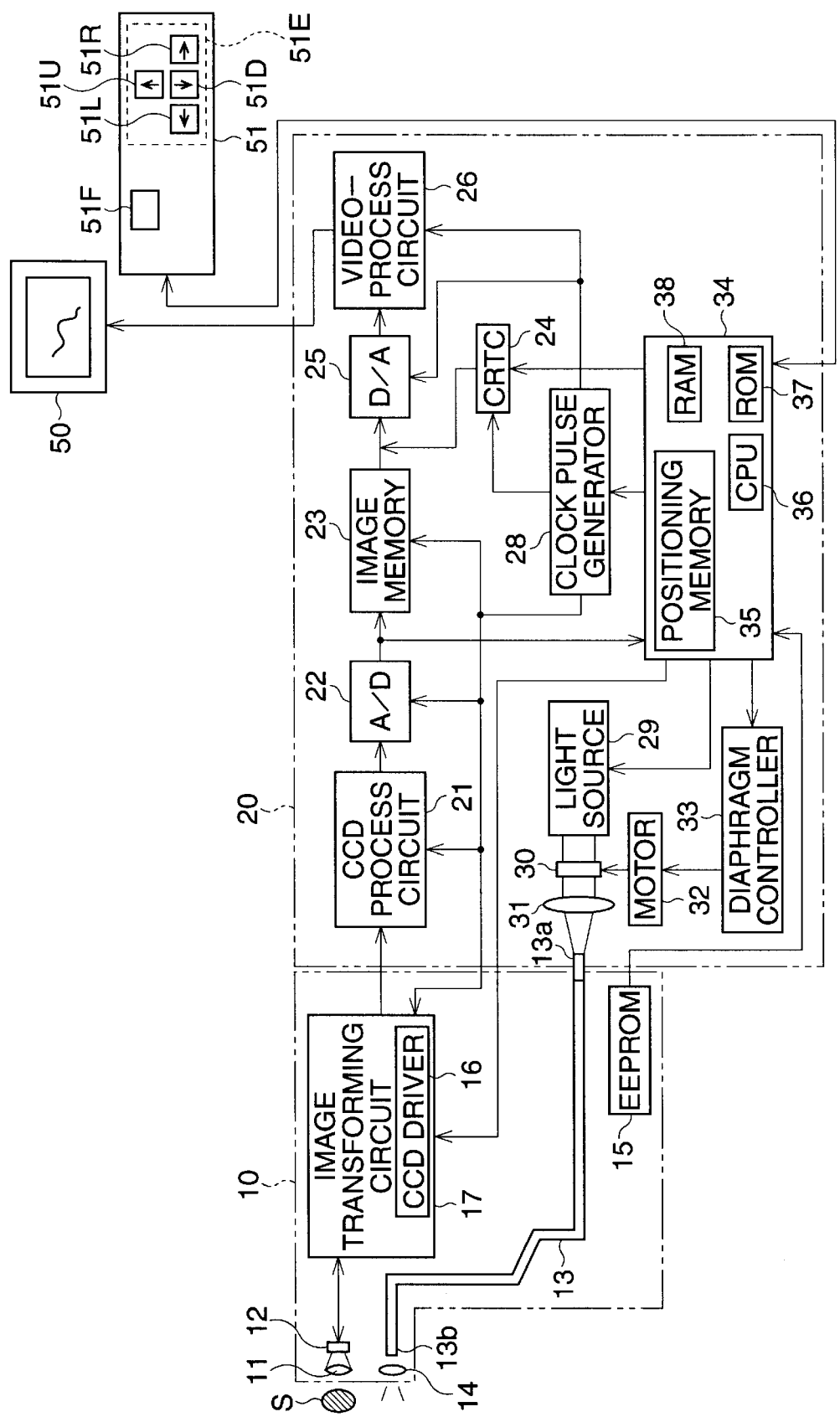
FIG. 1 is a block diagram of an electronic endoscope of a first embodiment.
Figure 2:
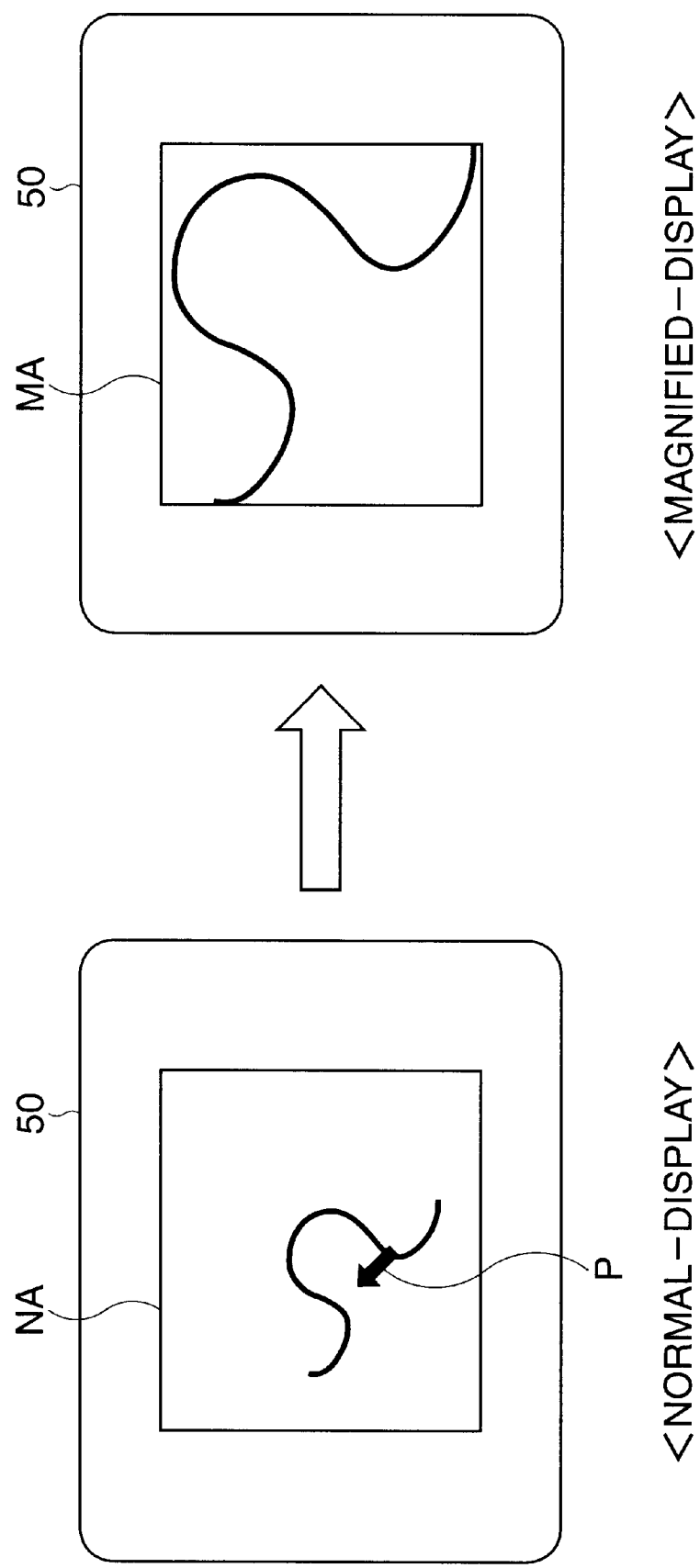
FIG. 2 is a view showing an image displayed on a monitor as a normal-display and a magnified-display.

FIG. 1 is a block diagram of an electronic endoscope of a first embodiment. FIG. 2 is a view showing an image displayed on a monitor.

In the electronic endoscope, a video-scope 10, a video-processor 20 and a TV monitor 50 are provided and the monitor 50 is connected to the video-processor 20. The video-scope 10 is detachably and interchangeably connected to the video-processor 20. The electronic endoscope is used when an operation, an inspection or a treatment for an organ, such as a stomach, is performed, with the video-scope 10 inserted into the body. A CPU 36, provided in a system control circuit 34 in the video-processor 20, controls the total electronic endoscope.

A light source 29 provided in the video-processor 20 radiates light, which is directed to an incidence surface 13a of a light guide 13 via a diaphragm (stop) 30 and a collective lens or condensing lens 31. Herein, the light source 29 is a halogen lamp. The light guide 13 provided in the video-scope 10 is a fiber-optic bundle, which guides the light from the light source 29 to the distal end of the video-scope 10. The light entering the incidence surface 13a passes through the light guide 13 and radiates from a distal end 13b of the light guide 13 toward a subject S, via a diffusion lens 14, so that subject S is illuminated.

Light reflected from the subject S reaches a CCD (Charge-Coupled Device) 12, which is an image sensor, via an objective lens 11, whereby the object image is formed on the CCD 12. A plurality of photo-sensors, or photodiodes (not shown herein) are arrayed on a light-receiving surface on the CCD 12, each photodiode corresponding to each pixel of the CCD 12. In this embodiment, an on-chip filter method is applied as a color photographing method, a one-chip complementary color filter (not shown herein) is arranged in front of the arrayed photodiodes. When the subject image is formed on the light-receiving surface of the CCD 12, analog image-pixel signals corresponding to light passing through the color filter are generated by photoelectric effect. Herein, the pixel number of the CCD 12 is approximately one million two hundred thousand (1,200,000).

In this embodiment, for a display-state, either a normal-display or a magnified-display is selected. Further, the NTSC method is applied as a video standard (video scanning standard) and the monitor 50 corresponds to the NTSC method. Therefore, resolution of the monitor 50, in other words, or the maximum number of pixels which can be used by the monitor 50 correspond to the NTSC method, i.e., approximately four hundred and ten thousand (410,000).

In the normal-display, as described below, image-pixel signals generated at 300,000 pixels in the CCD 12 are read from the CCD 12. An image transforming circuit17, including a CCD driver 16, forms an image to be displayed on the monitor 50 in accordance with an optical subject image formed on the CCD 12. The CCD 12 is driven by the CCD driver 16, driving signals fed to charge-transfer registers (not shown) in the CCD 12. In the normal-display, image-pixel signals (first image-pixel signals), generated at approximately three hundred thousand (300,000) pixels among 1,200,000 pixels, are read from the CCD 12. Namely, the driving signals for the charge-transfer registers are adjusted such that only charges generated at the 300,000 pixels are transferred to the charge-transfer registers. Thus, one frame/field worth of image-pixel signals corresponding to a subject image composed of the approximately 300,000 pixels are fed to the image transforming circuit 17 as color image signals. The image transforming circuit 17 controls the driving signals fed from the CCD driver 16 to the CCD 12 in accordance with a control signal fed from the system control circuit 34. The one frame worth of image-pixel signals are fed to a CCD process circuit 21 via the image transforming circuit 17. As the NTSC method is applied, the one frame (field) worth of the image-pixel signals are read from the CCD 12 in 1/30 (1/60) second intervals.

In the CCD-process circuit 21, some processes, such as a noise reduction, are applied to the input image-pixel signals. Further, the one frame worth of image-pixel signals are transformed into primary color image signals composed of red (R) signal components, green (G) signal components and (B) signal components, the primary color image signals being divided into the R, G, B signal components respectively. The analog primary color image signals are converted to digital color signals in an A/D converter 22. The digital color image signals are temporarily stored in an image-memory 23. The stored digital color image signals are fed from the image-memory 23 to a D/A converter 25, in which the digital image signals are converted to analog image signals. The analog image signals are fed to a video-process circuit 26, in which the analog image signals are transformed to video signals, such as NTSC composite signals.

In a CRTC (CRT controller) 24, which includes a character generator ROM (not shown), to display character information and an indicator mark, such as a pointer, on the monitor 50, character signals are generated and output. The character signals output from the CRTC 24 are superimposed upon the video signals output from the image-memory 23. In the system control circuit 34, character control signal for generating the character signals are output to the CRTC 24. The output timing of the character signals are adjusted by the system control circuit 34 such that the character information and/or the indicator mark are displayed at given positions.

The video signals are output to the monitor 50 in order, in accordance with the NTSC method, thus an observed image in the normal-display state is displayed within an image area NA on the monitor 50 (See FIG. 2). Hereinafter, this displayed observed image at the normal-display is represented by a "normal-image". A pixel number in the image-area NA is approximately three hundred thousand (300,000), which corresponds to the number of pixels, from which the image-pixel signals are read.

In an EEPROM (Electronic Erasable Programmable ROM) 15 provided in the video-scope 10, data associated with a type of the video-scope 10, such as the pixel number and the pixel array, is stored in advance. When the video-scope 10 is connected to the video-processor 20, the data is read from the EEPROM 15 and fed to the system control circuit 34. In the system control circuit 34, a positioning memory 35, CPU 36, ROM 37 and RAM 38 are provided, the data read from the EEPROM 15 is temporarily stored in the RAM 38. The size of the image area NA is predetermined in accordance with the pixel number of the CCD 12 and the video standard. The data associated with the image area NA and pixel array data of the CCD 12 is temporarily stored in the positioning memory 35.

In the normal-display, as shown in FIG. 2, a pointer P for indicating a specific portion in the normal-image is displayed. The operation for shifting an indicating position of the pointer P is performed by using the keyboard 51.

When a shift key 51E on the keyboard 51, composed of a shift-up key 51U, a shift-down key 51D, a shift-right key 51R and a shift-left key 51L, is operated, an operation-signal corresponding to the operated key is fed to the system control circuit 34. Based on the operation-signal, in which position data of the pointer P to be shifted is included, the character control signal is fed from the system control circuit 34 to the CRTC 24 such that the pointer P is shifted in a direction corresponding to the operated shift key. The pointer P is shifted in an up, down, left or right direction. A function key 51F is a key for changing the display-state, namely, interchanging the normal-display and magnified-display with each other. If the function key 51F is operated when the normal-image and the pointer P is displayed on the monitor 50, a magnified image, which is a magnified image of a specific portion, is displayed such that the position indicated by the pointer P becomes the center of the magnified image (See FIG. 2). Hereinafter, the image of the specific portion is represented by a "magnified-image". In this case, image-pixel signals generated at pixels corresponding to the magnified-image are read from the CCD 12 in accordance with the driving signals from the CCD driver 16 in the image transforming circuit 17. When the function key 51F is further operated, the magnified-display state is changed back to the normal-display state.

Note that, similar to a conventional electronic endoscope, the position of the pointer P is controlled by the system control circuit 34 so that the pointer P is not moved outside the image-area NA. The system control circuit 34, based on the data associated with the image-area NA stored in the positioning memory 35 and the operation-signal, feeds the control signal to the CRTC 24.

A clock pulse generator 28 outputs a clock pulse to each circuit, CCD-process circuit 21, image-memory 23, CRTC 24, video-process circuit 26, etc., thus input and output timing of signals in each circuit is controlled. In the CCD-process circuit 21, the luminance signals are generated from the image-pixel signals and fed to the system control circuit 34 via the A/D converter 22. Based on the luminance signals, a control signal for the diaphragm 30 is output from the system control circuit 34 to the diaphragm controller 33. A driving signal for driving a motor 32 is fed from the diaphragm controller 33 to the motor 32, so that the motor 32 drives and the diaphragm 30 opens or closes such that an amount of light illuminated at the subject S is controlled.

Figure 3:
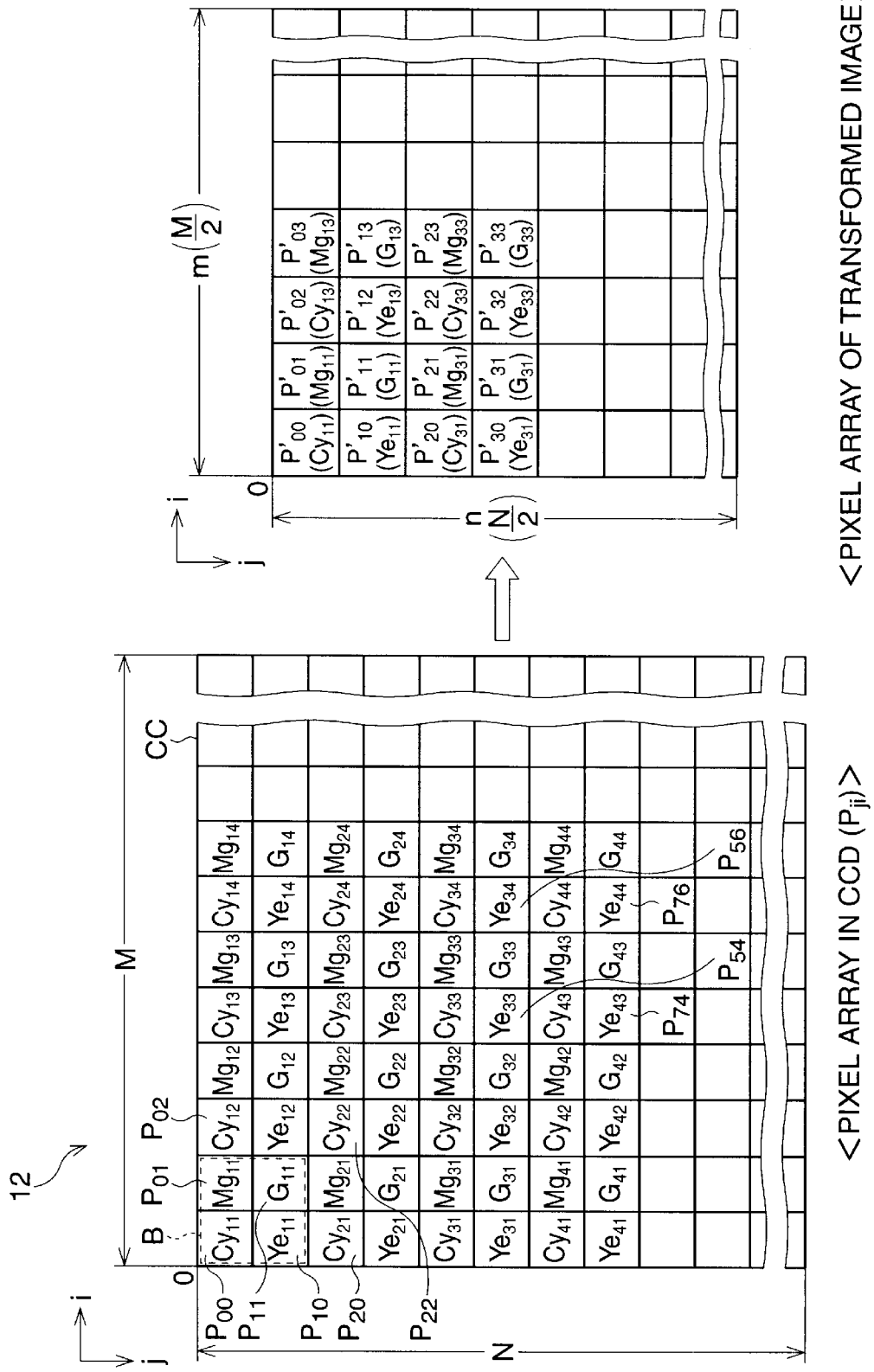
FIG. 3 is a conceptual view showing a down sampling.

FIG. 3 is a view partially showing a pixel array (photosensor array) in the CCD 12.

The complementary color filter "CC" provided on the CCD 12 is a mosaic color filter, checkered by cyan (Cy), Magenta (Mg), yellow (Ye) and green (G) colors. The color filter CC is partitioned into a plurality of blocks B, each of which is composed of four (Cy, MG, Ye, G) color elements. The array of the color filter CC corresponds to the pixel array of the CCD 12. In this embodiment, the interline-transfer method is applied as a charge-transfer method. Therefore, Vertical registers along columns in the pixel array are provided between a vertical pixel array and a neighboring vertical pixel array (not shown). Further, horizontal registers are arrayed below the pixel array (not shown). In FIG. 3, for ease of explanation, only the pixel array and the filter array are shown and each pixel is represented by "$P_{ji}$". Note that, a left corner of the pixel array is set as an origin, and suffix "j" indicates a pixel position along the vertical direction and suffix "i" indicates a pixel position along the horizontal direction. Then, in FIG. 3, the positions of the filter color elements are also represented by suffixes in each color element. At the pixel array, "M" pixels and "N" pixels are arranged along the horizontal direction and vertical direction respectively.

At the normal-display, a "down sampling", in other words, pixel-number transform or image-size transform is performed. Namely, as described above, approximately 300,000 pixels are sampled to form the subject image in the normal-display state. To sample the 300,000 pixels from the 1,200,000 pixels on the CCD 12, one pixel among four pixels corresponding to the neighboring four same color elements is sampled, and the charges generated at the sampled pixels only are transferred to the vertical registers. Charges generated in the remaining three pixels are not transferred to the vertical registers. This process is performed to the neighboring four pixels corresponding to the neighboring four same color elements, and is further performed to all of the color elements (Cy, Mg, Ye, G).

In FIG. 3, a pixel array composed of the sampled pixels (300,000 pixels) is shown. When the sampled pixel is represented by "$P'_{ji}$", "$P'_{ji}$" is obtained by one of following four formulae. Note that, similar to the pixel array in the CCD 12, suffix "j" and "i" indicate positions of the sampled pixels along the vertical and horizontal direction respectively.

$$P'_{ji}=P_{ji}(j<2,\ i<2) \tag{1}$$

$$P'_{ji}=P_{j+2,i}(j\geq 2,\ i<2) \tag{2}$$

$$P'_{ji}=P_{j,i+2}(j<2,\ i\geq 2) \tag{3}$$

$$P'_{ji}=P_{j+2,i+2}(j\geq 2,\ i\geq 2) \tag{4}$$

For example, among pixels $P_{00}$, $P_{02}$, $P_{20}$, $P_{22}$ corresponding to the neighboring cyan (Cy) color elements $Cy_{11}$, $Cy_{12}$, $Cy_{21}$, $Cy_{22}$, the pixel $P_{00}$ corresponding to the cyan color element $Cy_{11}$ is sampled as the pixel "$P'_{00}$" in accordance with the formula (1). Similarly, among pixels $P_{54}$, $P_{56}$, $P_{74}$, $P_{76}$ corresponding to the neighboring Yellow color elements $Ye_{33}$, $Ye_{34}$, $Ye_{43}$, $Ye_{44}$, the pixel $P_{54}$ corresponding to the yellow color element $Ye_{33}$ is sampled as the pixel "$P'_{32}$", in accordance with the formula (4). Note that, the formulae (1) to (4) are defined in accordance with the array of the color filter CC. Therefore, when another color element type (for example, R, G, B) or another array method of the color filter is applied, the formulae (1) to (4) are changed appropriately.

The down sampling is performed to the one million two hundred thousand pixels, so that the subject image on the CCD 12 is transformed to an image composed of approximately 300,000 pixels. At the pixel array of the transformed subject image, "m" and "n" pixels are arranged along the horizontal and vertical direction respectively. As the similitude factor is "¼", "m" and "n" is "M/2" and "N/2" respectively. Hereinafter, the subject image formed on the CCD 12, composed of all of pixels in the CCD 12, is represented by a "all-pixel subject image", whereas the subject image composed of the approximately 300,000 sampled pixels is represented by a "normal-display subject image".

Figure 4:
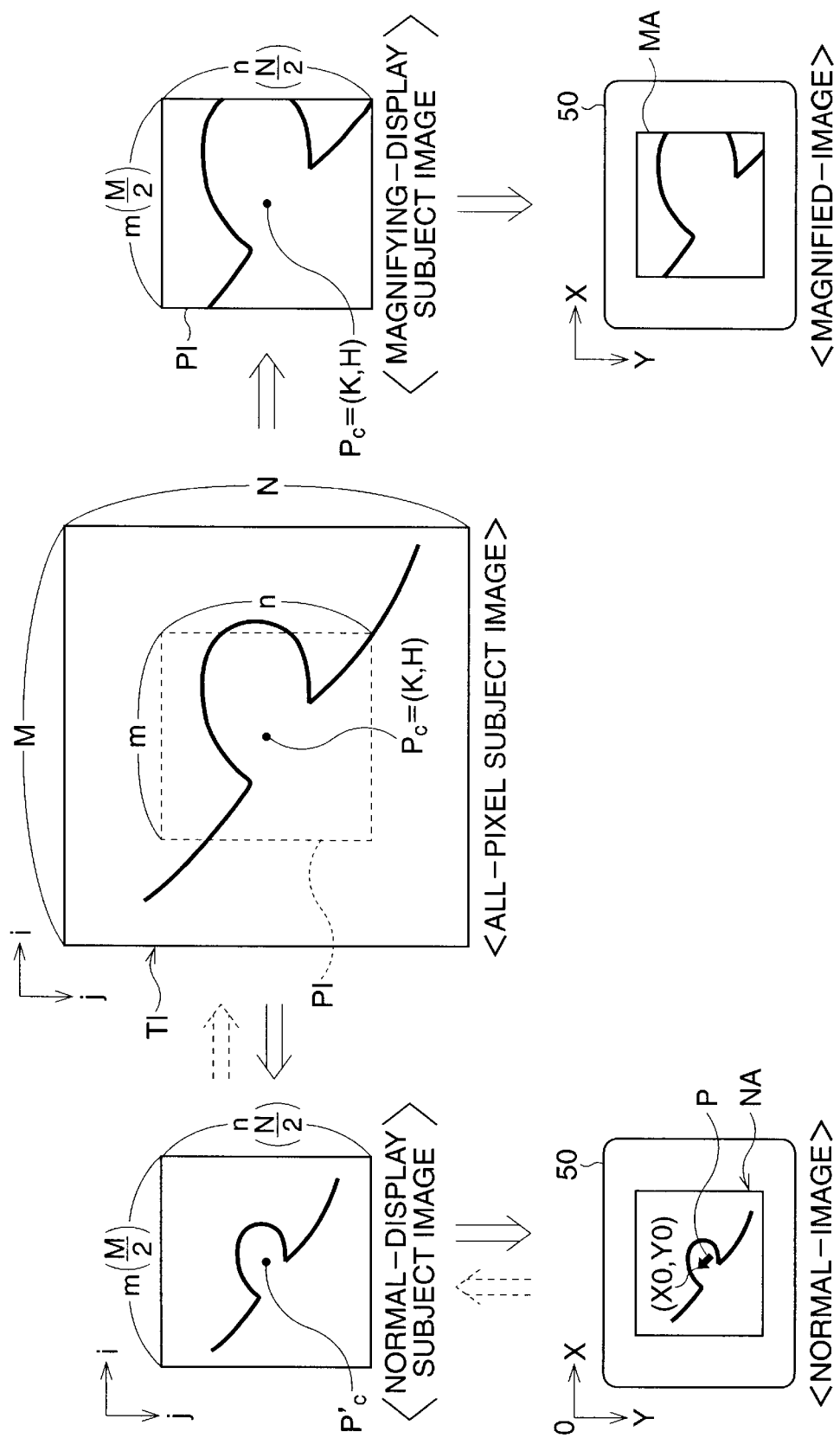
FIG. 4 is a view showing a magnifying process

FIG. 4 is a view showing a magnifying process. Herein, the position of the pointer P on the monitor 50 is represented by monitor-coordinates (X, Y). The "X" indicates the position along the horizontal direction and the "Y" indicates the position along the vertical direction. Note that, the apex of the arrow at the pointer P represents the indicating-pixel position. Herein, an area on the CCD 12, within which the all-pixel subject image is formed, is represented by an "image-forming area TI".

As described above, in the normal-display state, the all-pixel subject image formed on the CCD 12 is transformed to the normal-display subject image by the down sampling. Then, the normal-image is displayed on the monitor 50. On the monitor 50, the pointer P is positioned at given coordinates (X0, Y0) by operating the shift key 51E. In the system control circuit 34, the position of the pointer P is detected in accordance with the operation signal fed from the shift key 51E, which includes information of a shifted position of the pointer P.

When the operator depresses the function key 51F, the magnifying process as described below is performed.

Firstly, at the pixel array of the normal-display subject image, a pixel $P'_c$ corresponding to the position of the pointer P is detected in accordance with the coordinates (X0, Y0) and the image area data stored in the positioning memory 35. As shown in FIG. 3, the pixel $P'_{ji}$ at the normal-display subject image is obtained by one of the formulae (1) to (4). Therefore, a pixel in the all-pixel subject image corresponding to the pixel $P'_c$, in other words, the coordinates (X0, Y0) of the pointer P, is obtained using the formulae (1) to (4). Herein, the above pixel at the all-pixel subject image is represented by an "indicating-pixel $P_c$", and the position of the indicating-pixel $P_c$ in the image-forming area TI is represented by coordinates "(K, H)". Namely, "$P_c$" is "$P_{K,H}$".

Then, a part-area PI, which is a part of the image-forming area TI, is defined. The indicating-pixel $P_c$ becomes a center of the part-area PI. In this embodiment, a portion of the all-pixel subject image, corresponding to the part-area PI, is defined as an image formed at the magnified-display state. Hereinafter, the partial image composed of pixels arranged in the part-area PI is represented by a "magnified-display subject image". Further, in this embodiment, the size of the normal area NA on the monitor 50 is substantially equal to that of the magnified-area MA. Namely, the pixel-number of the magnified-display subject image is equal to that of the normal-display subject image. To form the magnified-display subject image, the part area PI, in which 300,000 pixels are arranged, is defined such that the indicating-pixel $P_c$ becomes the center of the part-area PI. The pixel number along the horizontal and vertical directions are "m (=M/2)" and "n (=N/2)" respectively. A control signal is fed from the system control circuit 34 to the image transforming circuit 17 in accordance with the pixel array data stored in the positioning memory 35, such that driving signals corresponding to the pixels for the magnified-display subject image are output to the CCD 12. Thus, only the image-pixel signals generated in the pixels within the part-area PI are read from the CCD 12 and the magnified-image is displayed within the image-area MA.

However, other similitude factors maybe applied. When the pixel number of the CCD 12 is "D", and the pixel number of the normal-display subject image is "U", the similitude factor is "D/U". The "U" is equal to and less than approximately 410,000. In this case, the formulae (1) to (4) are changed in accordance with the similitude factor. Note that, the inverse of the similitude factor maybe other integers (for example, ¼), similarly to the present embodiment, or may be a rational number (for example, ⅖). When these apply, down samplings corresponding to the other integers and rational number, which are conventionally known, are performed respectively. Further, to obtain a high-resolution normal image at the normal-display, the image forming processor may form the normal-display subject image by performing the "average-operation method" also conventionally known, which calculates an average of neighboring pixels corresponding to the neighboring same color elements.

Figure 5:
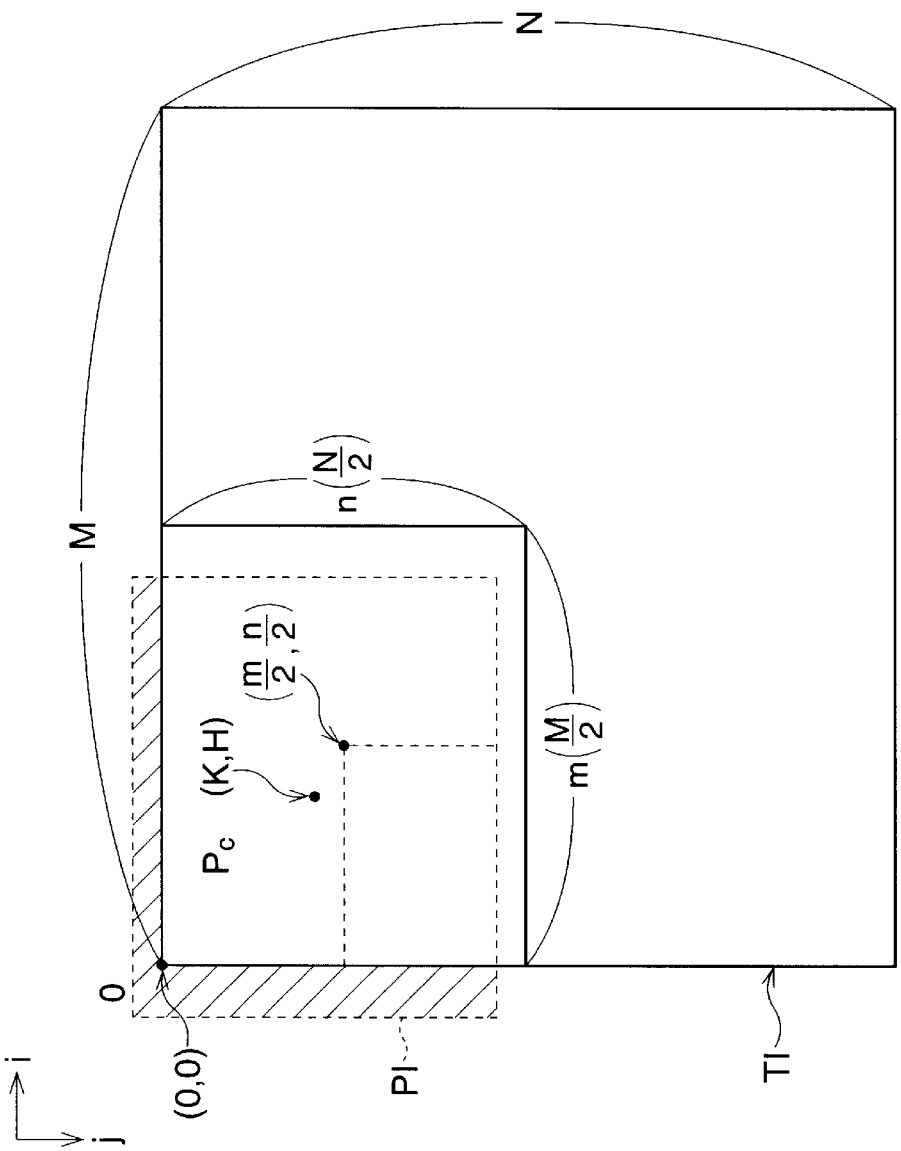
FIG. 5 is a view showing a restriction of a position of an indicating-pixel.

FIG. 5 is a view showing a restriction of the position of the indicating-pixel $P_c$.

As described above, the part-area PI has "m×n (=300,000)" pixels such that the center of the part-area PI becomes the indicating-pixel $P_c$. Namely, for the horizontal direction, "m/2" pixels are arranged along the positive direction from the position of the indicating-pixel $P_c$ and the negative direction from the position of the indicating-pixel $P_c$, respectively. Similarly, for the vertical direction, "n/2" pixels are arranged along the positive direction from the position of the indicating-pixel $P_c$ and the negative direction from the position of the indicating-pixel $P_c$, respectively. Therefore, when the indicating-pixel $P_c$, which is defined in accordance with the position of the pointer P, is located near the outline of the image-forming area TI, the part-area PI cannot be defined, namely, the magnified-display subject image cannot be formed. For example, as shown in FIG. 5, when the coordinate (K, H) of the indicating-pixel $P_c$ is nearer to the origin (0,0) than the coordinate (m/2, n/2), a portion of the part-area PI is out of the image-forming area TI, as shown by hatching.

Accordingly, in this embodiment, as described later, the image-forming area TI is divided into nine areas, and then the part-area PI is defined in accordance with the nine areas and the position of the indicating-pixel $P_c$.

Figure 6:
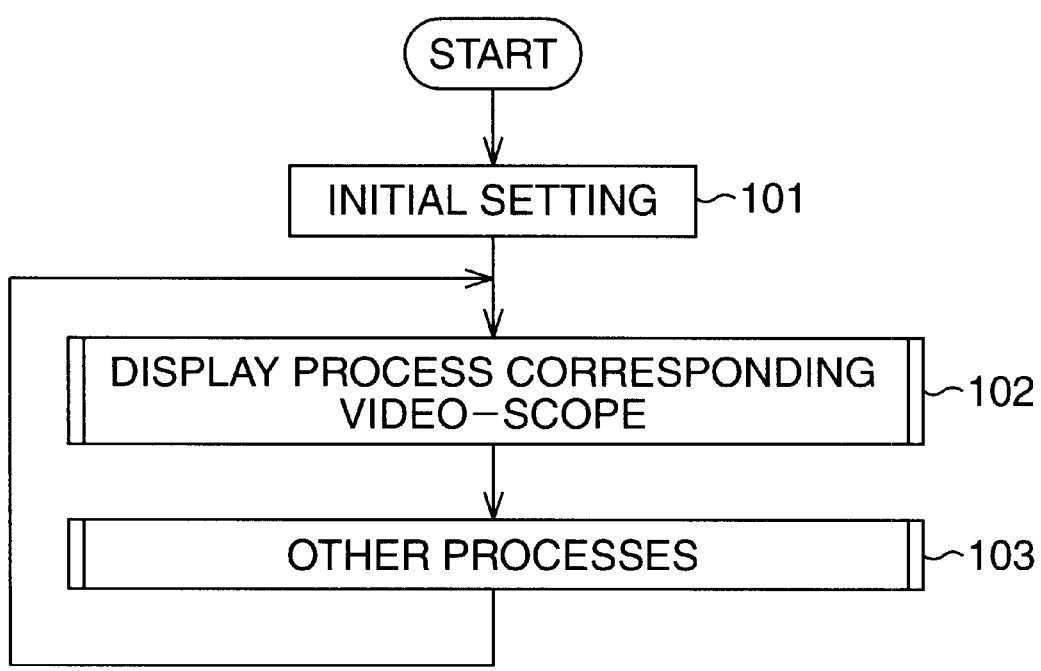
FIG. 6 is a flowchart showing a main routine associated with the operation of the electronic endoscope as a whole.

FIG. 6 is a flowchart showing a main routine associated with operation of the electronic endoscope as a whole, performed by the CPU 36 in the system control circuit 34. When the electric power is turned ON, the process is started.

In Step 101, the light source 29, the diaphragm 30, etc., are initially set. In Step 102, a display process corresponding to the video-scope 10 is performed. In Step 103, other processes, for example, date-display process, are performed. These operations of the electronic endoscope are performed until the electric power is turned OFF.

Figure 7:
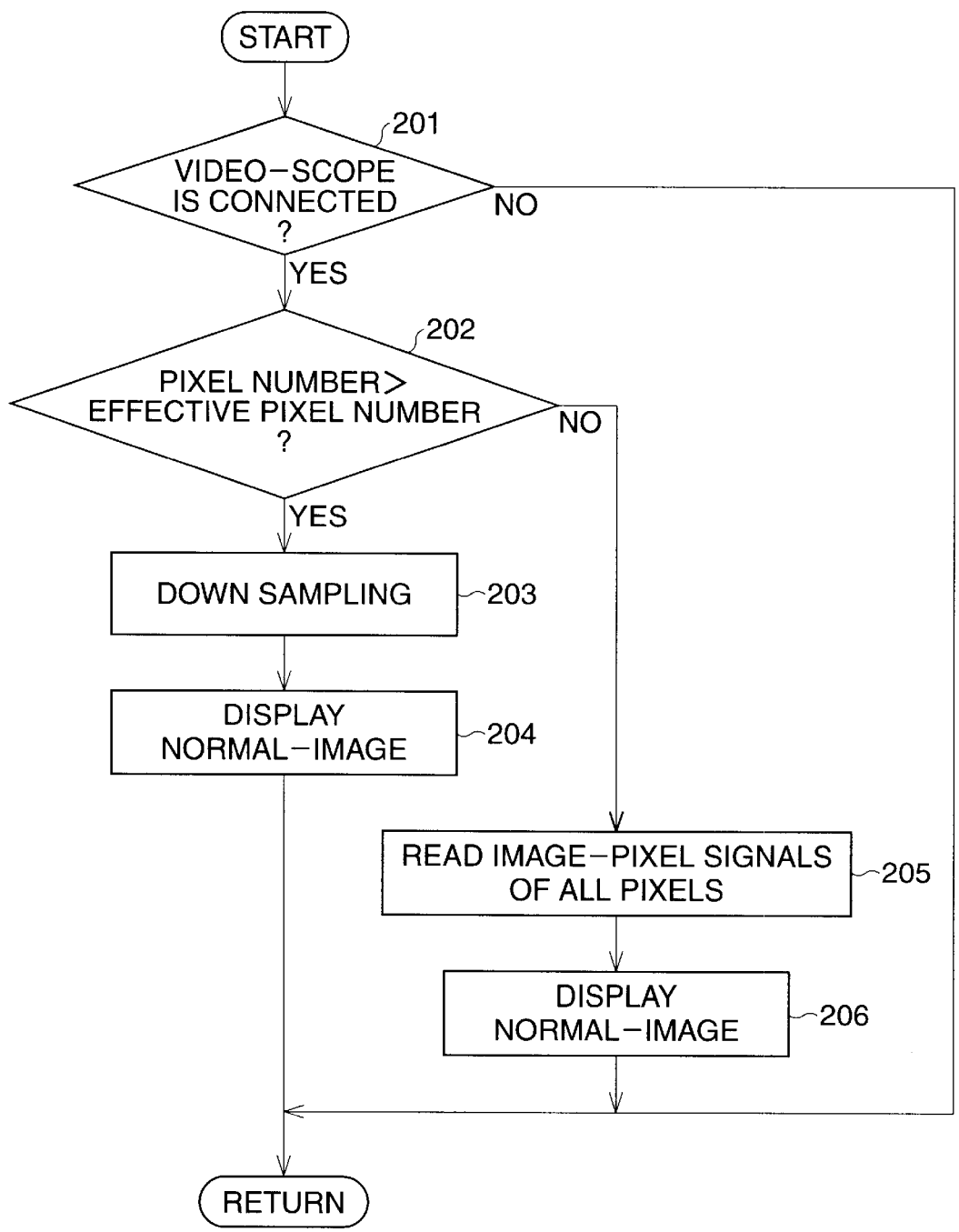
FIG. 7 is a flowchart showing a subroutine of a display process corresponding to a connected video-scope.

FIG. 7 is a view showing a subroutine of Step 102 in FIG. 6. The CCD 12 in the video-scope 10 shown in FIGS. 1 to 5 has approximately 1,200,000 pixels, however, other types of video-scopes, which have a different number of pixels respectively, may be connected to the video-processor 20. In this embodiment, when the pixel number of the CCD in the video-scope 10, connected to the video-processor 20, is equal to or less than the effective pixel number, the down sampling is not performed in the normal-display state and an interpolation process is performed in the magnified-display state.

In Step 201, it is determined whether the video-scope 10 is connected to the video-processor 20. When it is determined that the video-scope 10 is not connected to the video-processor 20, in other words, the video-scope is detached to change the type of video-scope, this subroutine is terminated. On the other hand, when it is determined that the video-scope 10 is connected to the video-processor 20, the process goes to Step 202. In Step 202, based on the data associated with the pixel number, which is read from the EEPROM 15 in the video-scope 10 connected to the video-processor 20, it is determined whether the pixel number of the CCD 12 is larger than the effective pixel number, which corresponds to the NTSC method (410,000 pixels).

When it is determined that the pixel number of the CCD 12 is larger than the effective pixel number at Step 202, the process goes to Step 203, wherein the down sampling, or the pixel number transform is performed. Namely, the image-pixel signals generated at pixels corresponding to the normal-display subject image are read from the CCD 12. In Step 204, the video signals are generated in accordance with the read image-pixel signals and are fed from the video-process circuit 26 to the monitor 50, whereby the normal-image corresponding to the normal-display subject image is displayed on the monitor 50. After Step 204 is performed, the subroutine is terminated.

On the other hand, when it is determined that the pixel number of the CCD 12 is not larger than the effective pixel number at Step 202, the process goes to Step 205. In Step 205, the image-pixel signals generated at all pixels of the CCD 12, being less than the effective pixel number, are read. Namely, in this case, the all-pixel subject image becomes the normal-display subject image. In Step 206, the video signals corresponding to the all-pixel subject image are generated and fed to the monitor 50, so that the normal-image is displayed on the monitor 50.

Figure 8:
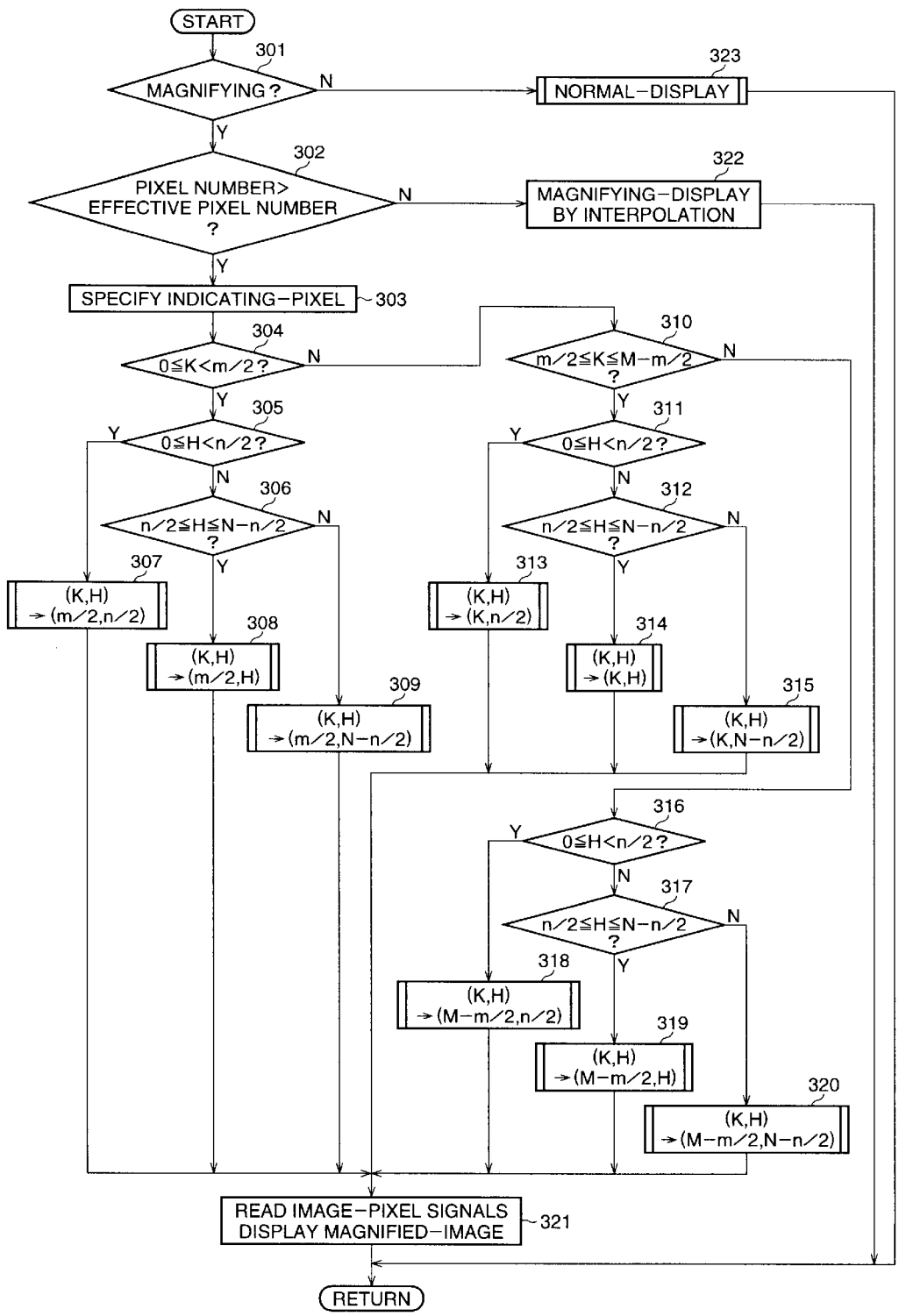
FIG. 8 is a flowchart showing an interrupt routine of a display changing process.
Figure 9:
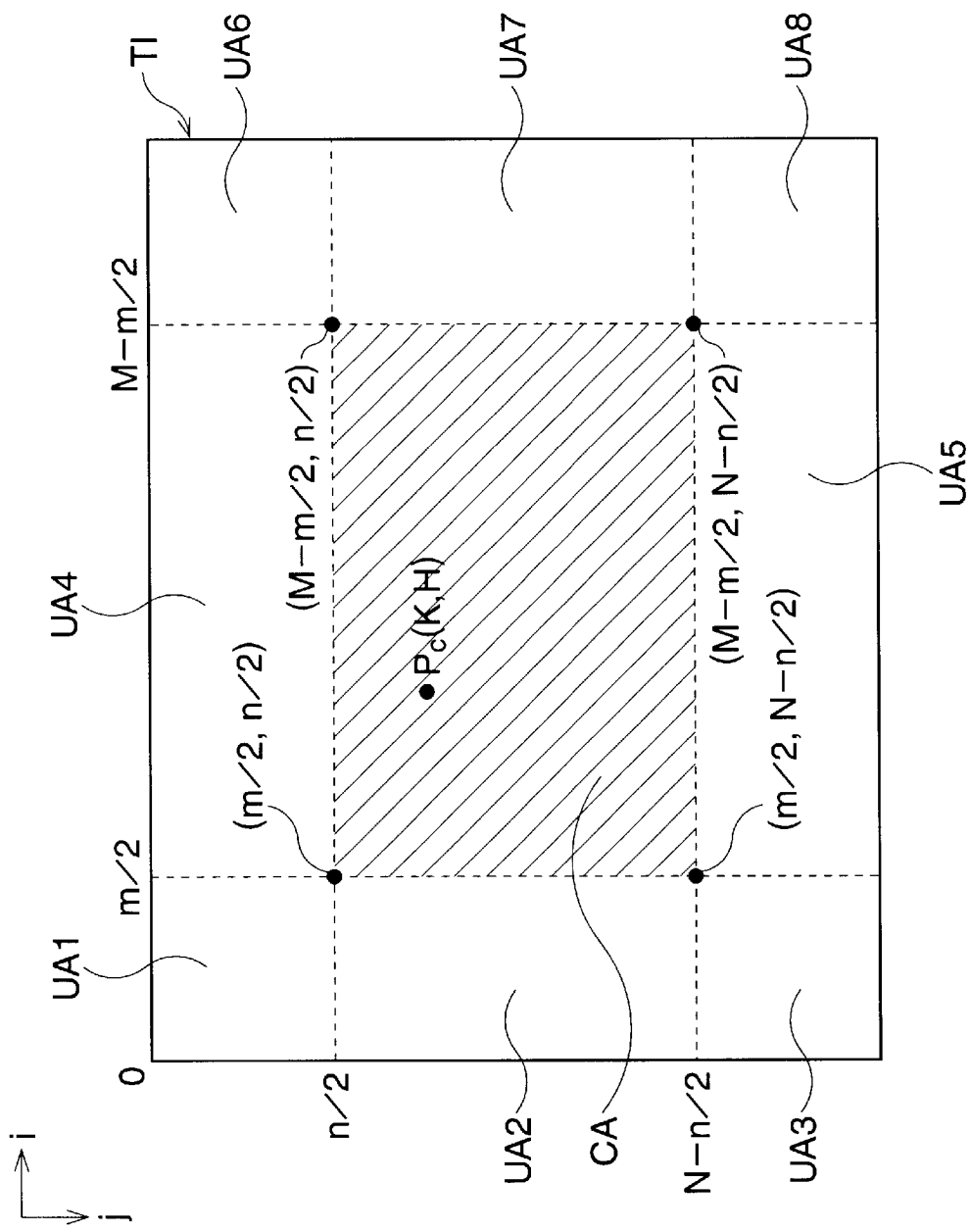
FIG. 9 is a view showing an image-forming area divided into nine areas.

FIG. 8 is a flowchart showing an interrupt routine of a magnifying/normal display changing process and FIG. 9 is a view showing the image-forming area TI. When the function key 51F on the keyboard 51 is depressed, this process is started by interrupting the main routine shown in FIG. 6.

In Step 301, it is determined whether the function key 51F is depressed when the display-state is the normal-display. Namely, it is determined whether the function key 51F is depressed to change the normal-display to the magnified-display.

When it is determined that the function key 51F is depressed when the display-state is the normal-display at Step 301, the process goes to Step 302. In Step 302, it is determined whether the pixel number of the CCD 12 in the video-scope 10 exceeds the effective pixel number of approximately 410,000 pixels.

When it is determined that the pixel number of the CCD 12 in the video-scope 10 exceeds the effective pixel number at Step 302, the process goes to Step 303, wherein the monitor-coordinates (X0, Y0) representing the position of the pointer P is detected. Then, based on the monitor-coordinate (X0, Y0), the indicating-pixel $P_c$ on the image-forming area TI is specified and the coordinate (K, H) of the indicating-pixel $P_c$ on the image-forming area TI is obtained, as indicated above. After Step 303 is performed, the process goes to Step 304.

As shown in FIG. 9, the image-forming area TI is partitioned into nine areas UA1, UA2, UA3, UA4, UA5, UA6, UA7, UA8 and CA. When the indicating-pixel $P_c$ is in the area CA, the part-area PI having "m×n" pixels can be defined such that the indicating-pixel $P_c$ becomes the center of the part-area PI. On the other hand, when the indicating-pixel $P_c$ is in one of other areas UA1 to UA8, the indicating-pixel $P_c$ to be the center of the part-area PI is changed to a modified pixel $P'_c$, which is located on the outline of the area CA. Then, the part-area PI, the center of which is the modified indicating-pixel $P''_c$, is defined.

In Step 304, it is determined whether the coordinate "K" along the horizontal direction satisfies the following formula.

$$0 < K < m/2 \qquad (5)$$

Namely, it is determined whether the indicating-pixel $P_c$ is located in one of the areas UA1, UA2 and UA3.

When it is determined that the formula (5) is satisfied, the process goes to Step 305, wherein it is determined whether the coordinate "H" along the vertical direction satisfies the following formula.

$$0 \leq H < n/2 \qquad (6)$$

Namely, it is determined whether the position of indicating-pixel $P_c$ is in the area UA1.

When it is determined that the formula (6) is satisfied at Step 305, namely, the position of indicating-pixel $P_c$ is in the area UA1, the process goes to Step 307. In Step 307, to define the part-area PI having "m×n" pixels, the indicating pixel $P_c$ is changed to a pixel located at the coordinates (m/2, n/2), which is defined as the modified indicating-pixel $P''_c$. After Step 307 is performed, the process goes to Step 321.

On the other hand, when it is determined that the formula (6) is not satisfied at Step 305, the process goes to Step 306. In Step 306, the coordinate "H" along the vertical direction satisfies the following formula.

$$0/2 \leq H \leq N - n/2 \qquad (7)$$

Namely, it is determined whether the position of indicating-pixel $P_c$ is in the area UA2.

When it is determined that the formula (7) is satisfied at Step 306, namely, the position of indicating-pixel $P_c$ is in the area UA2, the process goes to Step 308. In Step 308, to define the part-area PI having "m×n" pixels, the indicating pixel $P_c$ is changed to a pixel located at the left-side outline of the area CA, namely, at the coordinates (m/2, H), which is defined as the modified indicating-pixel $P''_c$. After Step 308 is performed, the process goes to Step 321.

On the other hand, when it is determined that the formula (7) is not satisfied at Step 306, namely, it is determined that the indicating-pixel $P_c$ is in the area UA3, the process goes to Step 309. In Step 309, to define the part-area PI having "m×n" pixels, the indicating pixel $P_c$ is changed to a pixel located at the coordinates (m/2, N−n/2), which is defined as the modified indicating-pixel $P''_c$. After Step 309 is performed, the process goes to Step 321.

When it is determined that the formula (6) is not satisfied at Step 304, namely, the position of indicating-pixel $P_c$ is not in one of the area UA1, UA2 and UA3, the process goes to Step 310. In Step 310, it is determined whether the coordinate "K" along the horizontal direction satisfies the following formula.

$$M/2 \leq K \leq M - m/2 \qquad (8)$$

Namely, it is determined whether the indicating-pixel $P_c$ is located in one of the areas UA4, UA5 and CA.

When it is determined that the formula (8) is satisfied at Step 310, the process goes to Step 311, wherein it is determined whether the coordinate "H" along the vertical direction satisfies the following formula.

$$0 \leq H < n/2 \qquad (9)$$

Namely, it is determined whether the position of indicating-pixel $P_c$ is in the area UA4.

When it is determined that the formula (9) is satisfied at Step 311, namely, the position of indicating-pixel $P_c$ is in the area UA4, the process goes to Step 313. In Step 313, to define the part-area PI having "m×n" pixels, the indicating pixel $P_c$ is changed to a pixel located at the upper-outline of the area CA, namely, at the coordinates (K, n/2), which is defined as the modified indicating-pixel $P''_c$. After Step 313 is performed, the process goes to Step 321.

On the other hand, when it is determined that the formula (9) is not satisfied at Step 311, the process goes to Step 312. In Step 312, the coordinate "H" along the vertical direction satisfies the following formula.

$$n/2 \leq H \leq N - n/2 \qquad (10)$$

Namely, it is determined whether the position of indicating-pixel $P_c$ is in the area CA.

When it is determined that the formula (10) is satisfied at Step 312, the process goes to Step 314, wherein the indicating-pixel Pc at the coordinates (K, H) is not changed and is directly defined as the center of the part-area PI. After Step 314 is performed, the process goes to Step 321. On the other hand, when it is determined that the formula (10) is not satisfied at Step 312, namely, it is determined that the indicating-pixel $P_c$ is in the area UA5, the process goes to Step 315. In Step 315, to define the part-area PI having "m×n" pixels, the indicating pixel $P_c$ is changed to a pixel located at the lower-outline of the area CA, namely, at the coordinate (K, N–n/2), which is defined as the modified indicating-pixel $P''_c$. After Step 315 is performed, the process goes to Step 321.

When it is determined that the formula (8) is not satisfied at Step 310, namely, the position of indicating-pixel $P_c$ is not in one of the areas UA4, UA5 and CA but in one of the areas UA6, UA7 UA8, the process goes to Step 316. In Step 316, it is determined whether the coordinate "H" along the horizontal direction satisfies the following formula.

$$0 \leq H < n/2 \tag{11}$$

Namely, it is determined whether the position of indicating-pixel $P_c$ is in the area UA6.

When it is determined that the formula (11) is satisfied at Step 316, namely, the position of indicating-pixel $P_c$ is in the area UA6, the process goes to Step 318. In Step 318, to define the part-area PI having "m×n" pixels, the indicating pixel $P_c$ is changed to a pixel located at the coordinate (M–m/2, n/2), which is defined as the modified indicating-pixel $P'_c$. After Step 318 is performed, the process goes to Step 321.

On the other hand, when it is determined that the formula (11) is not satisfied at Step 316, the process goes to Step 317. In Step 317, the coordinate "H" along the horizontal direction satisfies the following formula.

$$n/2 \leq H \leq N-n/2 \tag{12}$$

Namely, it is determined whether the position of indicating-pixel $P_c$ is in the area UA7.

When it is determined that the formula (12) is satisfied at Step 317, namely, the position of indicating-pixel $P_c$ is in the area UA7, the process goes to Step 319. In Step 319, to define the part-area PI having, "m×n" pixels, the indicating pixel $P_c$ is changed to a pixel located at the right-side outline of the area CA, namely, at the coordinates (M–m/2, H), which is defined as the modified indicating-pixel $P''_c$. After Step 319 is performed, the process goes to Step 321.

On the other hand, when it is determined that the formula (12) is not satisfied at Step 317, namely, it is determined that the indicating-pixel $P_c$ is in the area UA8, the process goes to Step 320. In Step 320, to define the part-area PI having "m×n" pixels, the indicating pixel $P_c$ is changed to a pixel located at the coordinates (M–m/2, N–n/2), which is defined as the modified indicating-pixel $P''_c$. After Step 320 is performed, the process goes to Step 321.

In Step 321, based on the indicating-pixel $P_c$ or the modified indicating-pixel $P''_c$, the image-pixel signals generated at the pixels within the part-area PI are read from the CCD 12 and the magnified-display is displayed on the monitor 50 in accordance with the read image-pixel signals. After Step 321 is performed, this routine is terminated.

On the other hand, when it is determined that the pixel number of the CCD 12 is not larger than the effective pixel number, at Step 302, the process goes to Step 322. In Step 322, image-pixel signals generated at all pixels in the CCD 12 are read from the CCD 12, and the interpolation process is performed at the image memory 23. Thus, the magnified-image formed by the interpolation process is displayed on the monitor 50.

When it is determined that the function key 51F is not depressed at Step 301, namely, it is determined whether the function key 51F is depressed to change the magnified-display to the normal-display, the process goes to Step 323. In Step 323, the normal-display, corresponding to the normal-display subject image, is displayed on the monitor 50. After Step 323 is performed, this routine is terminated.

Figure 10:
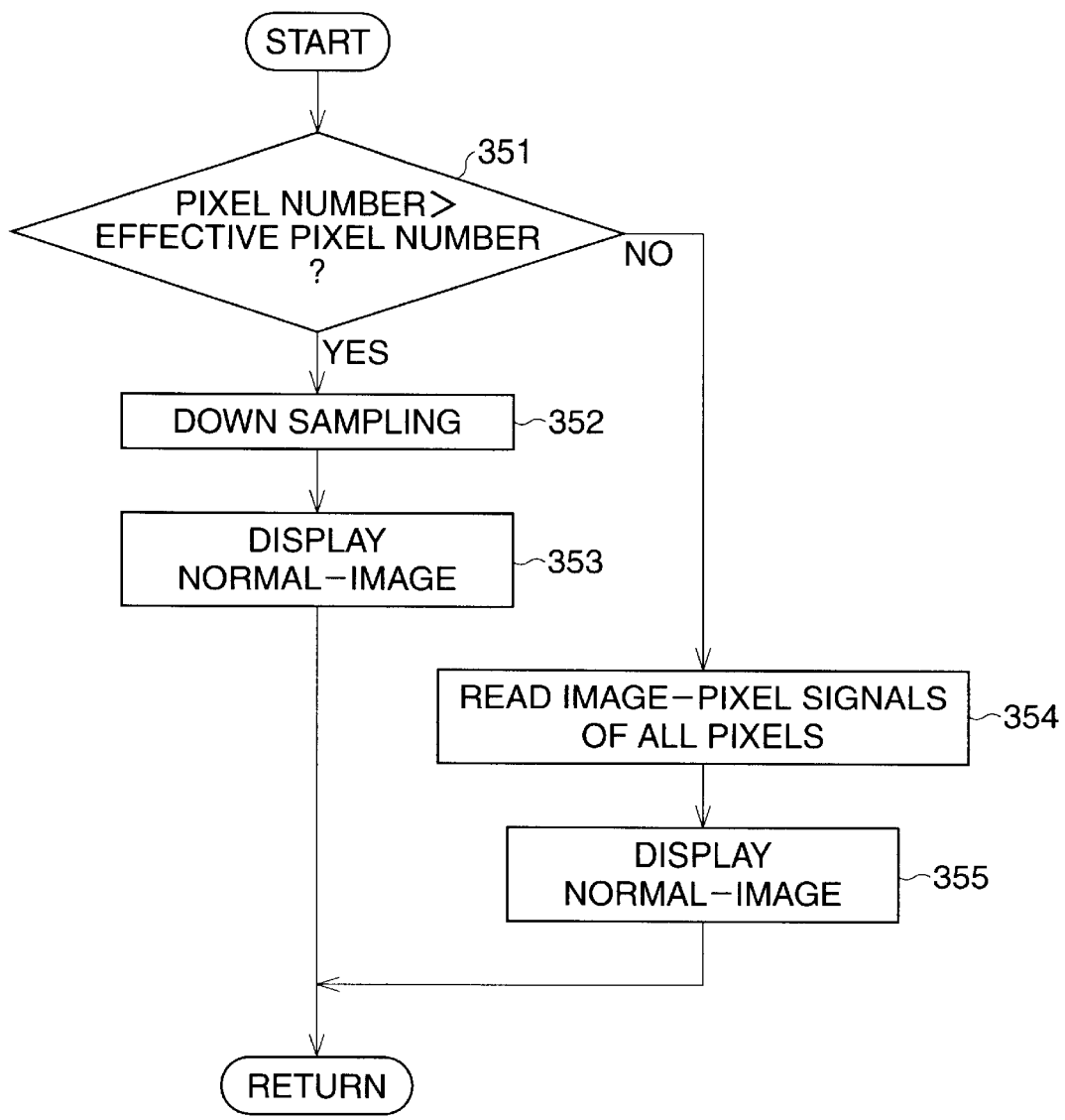
FIG. 10 is a flowchart showing a subroutine of the display process.

FIG. 10 is a flowchart of a subroutine of Step 323 in FIG. 8.

Performance of Steps 351 to 355 correspond to the performance of Steps 202 to 206 in FIG. 7. Namely, the down sampling is performed when the pixel number is larger than the effective pixel number, whereas all of the image-pixel signals generated at the CCD 12 are read from the CCD 12 when the pixel number is not larger.

In this way, in the first embodiment, when the display-state is the normal-display, the normal-image corresponding to the normal-display subject image is displayed on the monitor 50. The normal-display subject image composed of given pixels (for example, 300,000 pixels), which is equal to and less than 410,000 pixels, is formed by applying the down sampling to the all-pixel subject image composed of all of the pixels (herein, 1,200,000 pixels) in the CCD 12. The image-pixel signals corresponding to the normal-display subject image are read from the CCD 12. Further, when the display state is changed to the magnified-display, a magnified-image corresponding to the magnified-display subject image is displayed on the monitor 50. The magnified-display subject image composed of the approximately 300,000 pixels is formed by defining the part-area PI in the image-forming area TI. The image-pixel signals corresponding to the pixels arranged in the part-area PI are read from the CCD 12. On the other hand, when the pixel number of the CCD 12 is equal to or less than the effective pixel number, the normal-display subject image is formed form all of the pixels in the CCD 12, namely, the down sampling is not performed.

Note that, the size of the image area NA may be different from that of the image area MA. Namely, the pixel number of the normal-display subject image in the normal-display subject image may be different from that of the magnified-display subject image in the magnified-display.

For charge-transfer, another method, for example, a frame-transfer method, may be applied in place of the interline-transfer method. Further, a C-MOS image sensor may be applied in place of the CCD.

In this embodiment, the normal-display and magnified-display subject images are formed by reading image-pixel signals generated at corresponding pixels respectively. However, image-pixel signals generated at all of pixels may be read from the CCD 12 to the image forming circuit 17 and the normal-display and magnified-display subject images may be formed by reading only corresponding image-pixel signals.

In this embodiment, the NTSC method is applied as the video standard, however, other methods, such as the PAL method may be applied and further, computer video standards, such as the VGA and SVGA standards, may be applied. In which case the video signals are generated in accordance with the video standard and the resolution of the monitor depends upon the video standard.

In this embodiment, the video signals are generated in the video-processor, however, the video signals may be generated in the video-scope. In this case, each circuit for processing the image signals in the video-processor is provided in the video-scope.

Figure 11:
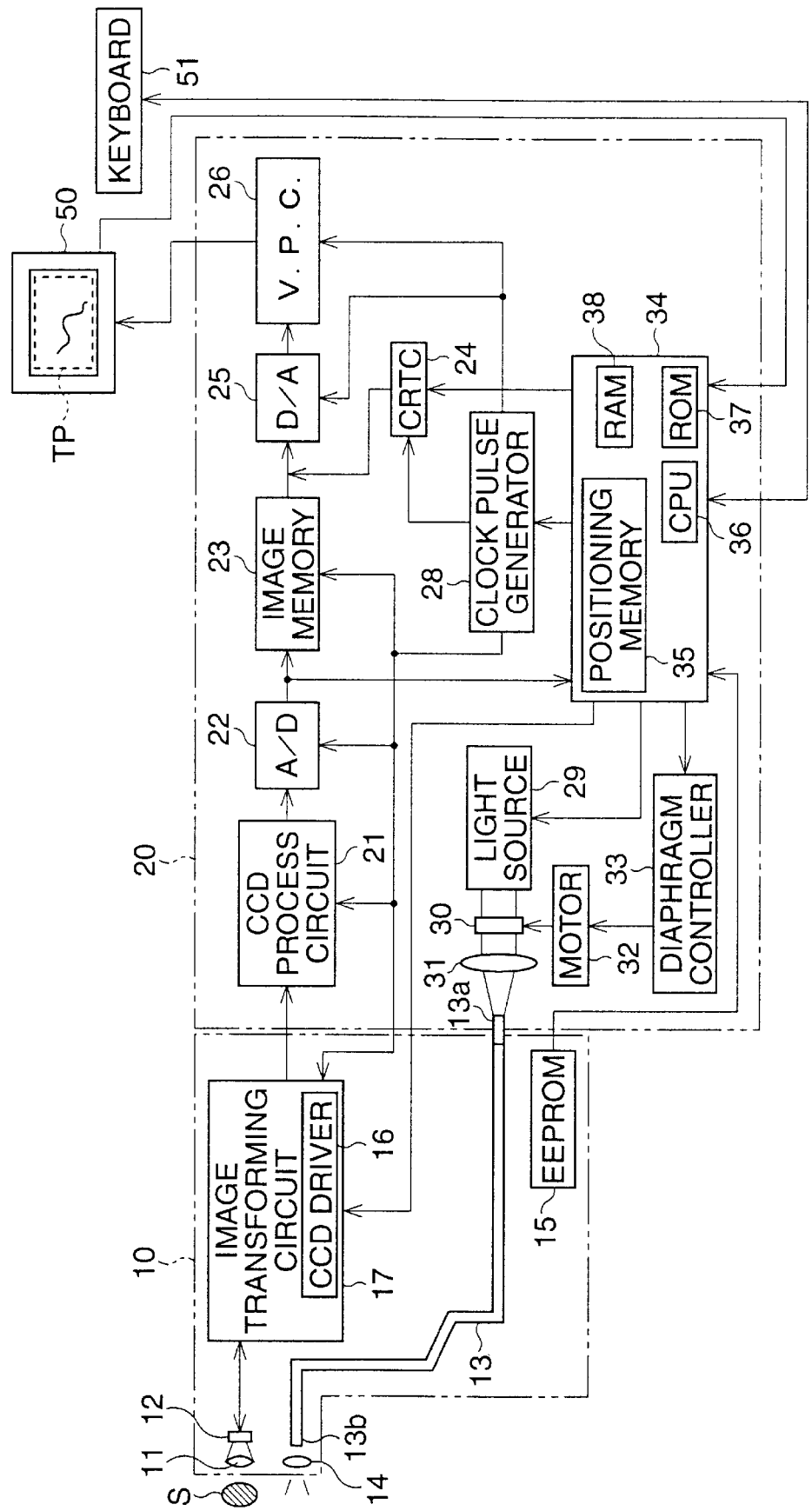
FIG. 11 is a block diagram of an electronic endoscope of a second embodiment.

FIG. 11 shows an electronic endoscope of a second embodiment. The second embodiment is different from the first embodiment in that a touch panel (touch screen) is applied instead of the shift key 51E and the function key 51F on the keyboard 51. Since other portions are similar to those of the first embodiment, the designation of the other portions remains the same and the description is omitted.

On the monitor 50, a transparent and colorless touch panel TP is provided, in which an electrode is arranged in a matrix. The image displayed on the monitor 50 is observed via the touch panel TP. The touch panel TP is an input device for selecting a given position on the screen of the monitor 50, which is indicated by the operator's finger. A signal corresponding to the indicated position is fed to the video-processor 20. In this embodiment, based on the coordinates (X, Y) on the monitor 50 corresponding to the touched position, the indicating-pixel $P_c$ is specified. When the operator touches the touch panel TP covering the screen of the monitor 50, an operation signal associated with the coordinates of the monitor 50, corresponding to the touched position on the touch panel TP, is fed to the system control circuit 34 via an interface (not shown). In the system control circuit 34, the touched, or indicated position is identified. Note that, an infrared radiation method is applied for detecting the touched position.

Similar to the first embodiment, in the positioning-memory 35, display-area (herein, the image-area NA) data corresponding to the pixel number of the CCD 12 in the video-processor 10 is stored, and then it is determined by the system control circuit 34 whether the touched position is in the image-area NA (See FIG. 2). When the touched position is in the image-area NA, the magnifying process similar to the first embodiment is performed. At this time, a pixel corresponding to the touched position is defined to a center of the magnified-display subject image. On the other hand, when the touched position is outside the image-area NA, the magnifying process is not performed. When a given position (for example, corner end) on the touch panel TP is touched when the magnified-image is displayed, the display-state is changed from the magnified-display to the normal-display.

Figure 12:
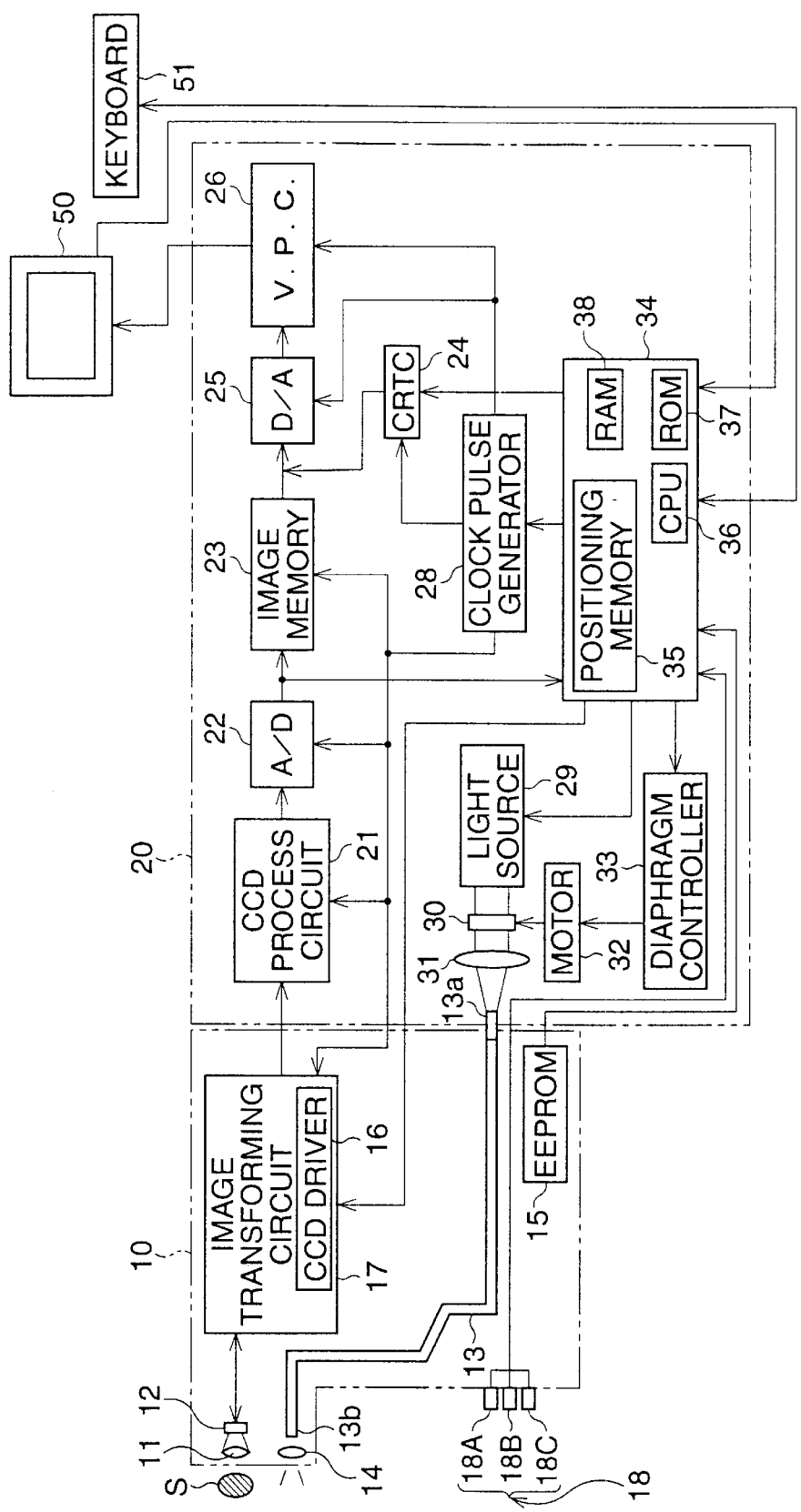
FIG. 12 is a block diagram of an electronic endoscope of a third embodiment.
Figure 13:
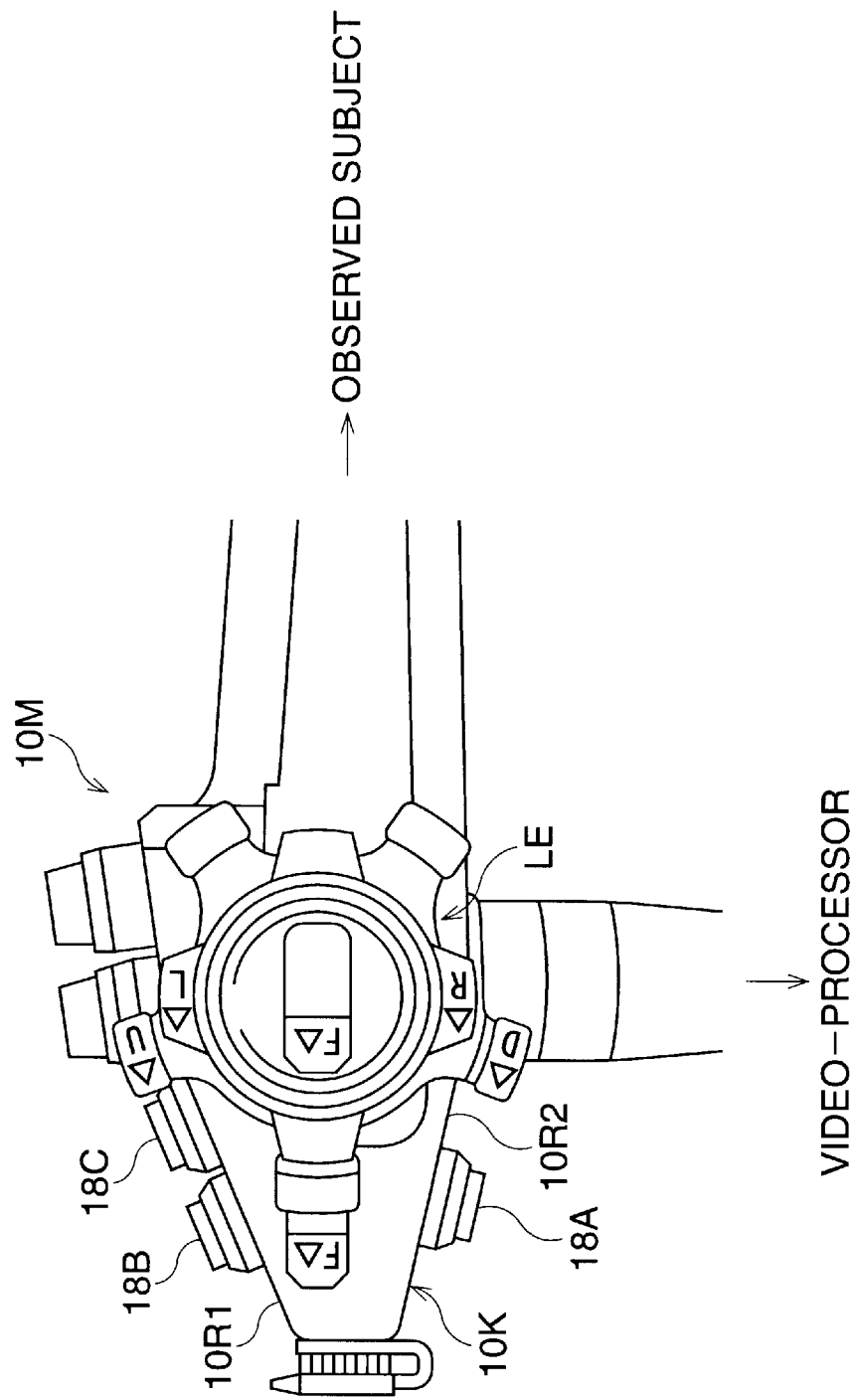
FIG. 13 is a view showing a manipulating section of a video-scope.
Figure 14:
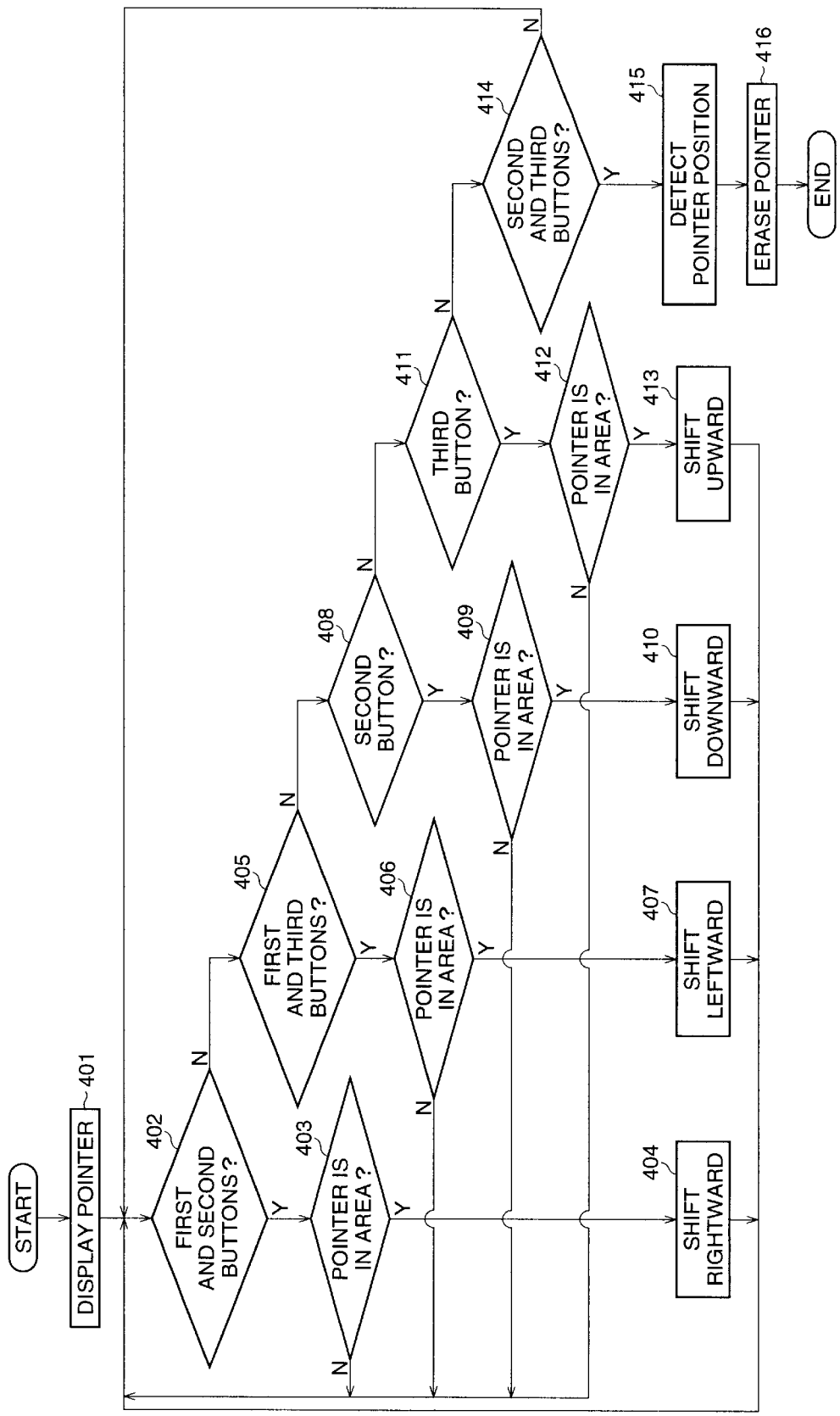
FIG. 14 is a flowchart showing a process for shifting a pointer.

FIGS. 12 to 14 show an electronic endoscope of a third embodiment. The third embodiment is different from the first embodiment in that an apparatus for shifting the position of the pointer P is provided at the video-scope. Since other portions are similar to those of the first embodiment, the designation of the other portions remains the same and the description is omitted.

FIG. 12 is a block diagram of an electronic endoscope of the third embodiment.

A pointer-shift button 18 composed of first pointer-shift button 18A, second pointer-shift button 18B and third pointer-shift button 18C are push buttons and are provided at the video-scope 10. The first, second and third pointer-shift buttons 18A, 18B and 18C are buttons for shifting the position of the pointer P in an up, down, right or left direction and for changing the display-state. When the first, second and third pointer-shift buttons 18A, 18B, 18C are operated, an operation signal associated with the position of the pointer P to be shifted is fed to the system control circuit 34 in the video-processor 20.

In the system control circuit 34, to change the position of the pointer P, a control signal is fed to the CRTC 24 in accordance with the operation signal from the pointer-shift button 18. In the CRTC 24, the output timing of the character signal corresponding to the pointer P is adjusted in accordance with the control signal from the system control circuit 34.

FIG. 13 is a view showing a part of the video-scope 10.

The video-scope 10 has a manipulating section 10M, in which various buttons including the pointer-shift button 18 are provided. The operator manipulates the distal end of the video-scope 10 using the manipulating section. For example, a rotational lever LE for bending the distal end of the video-scope 10 is manipulated by the operator's right hand. An end portion 10K at the manipulating section 10M tapers along one direction. When the operator holds the manipulating section 10M in the video-scope 10, a first surface 10R1 faces a vertical-up direction and a second surface 10R2 faces a vertical-down direction, as shown in FIG. 13.

The first pointer-shift button 18A is provided on the second surface 10R2 such that the operator can handle the button 18A by the left hand thumb, whereas the second, third surface 18B, 18C are provided on the first surface 10R1, such that the operator can handle the button 18B, 18C by the left hand index finger and middle finger respectively. The first pointer-shift button 18A and the second, third pointer-shift button 18B, 18C are opposite each other. The arrangement of the first, second and third pointer-shift button 18A, 18B, 18C and the end portion 10K are defined such that the operator can depress the first, second and third pointer-shift buttons 18A, 18B, 18C simultaneously.

In the embodiment, the first and second pointer-shift buttons 18A, 18B are depressed simultaneously when shifting the pointer P to the right, whereas the first and third pointer-shift buttons 18A, 18C are depressed simultaneously when shifting the pointer P to the left. Then, the second pointer-shift button 18B is depressed when shifting the pointer P down, whereas the third pointer-shift button 18C is depressed when shifting the pointer P up. Further, The second and third pointer-shift buttons 18B, 18C are depressed simultaneously when exchanging the display-state.

FIG. 14 is flow char to fan interrupt routine of the pointer shifting process. The first pointer-shift button 18A has a function further, which displays or undisplays the pointer P. When the first pointer-shift button 18A is depressed, the interrupt routine is started.

In Step 401, the control signal is fed from the system control circuit 34 to the CRTC 24 such that the pointer P is displayed at a given position. In Step 402, it is determined whether the first and second pointer-shift buttons 18A, 18B are depressed simultaneously to shift the position of the pointer P rightward by one coordinate worth.

When it is determined that the first, second pointer-shift buttons 18A, 18B are depressed simultaneously at Step 402, the process goes to Step 403, wherein it is determined whether the position of the pointer P is within the image-area NA. When it is determined that the position of the pointer P is within the image-area NA, the process goes to Step 404, wherein the pointer P is shifted rightward by one coordinate worth. After Step 404 is performed, the process returns to Step 402. On the other hand, when it is determined that the position of the pointer P is not within the image-area NA but on the right-side outline of the image-area NA, the process returns to Step 402 without shifting the pointer P, so that the pointer P remains within the image-area NA.

On the other hand, when it is determined in Step 402 that the first and second pointer-shift buttons 18A, 18B are not depressed simultaneously, the process goes to Step 405. In Step 405, it is determined whether the first and third pointer-shift buttons 18A, 18C are depressed simultaneously. When it is determined that the first and third pointer-shift buttons 18A, 18C are depressed simultaneously, the process goes to Step 406, wherein it is determined whether the position of the pointer P is within the image-area NA. When it is determined that the position of the pointer P is within the image-area NA, the process goes to Step 407, wherein the pointer P is shifted left ward by one coordinate worth. After Step 407 is performed, the process returns to Step 402. On the other hand, when it is determined at Step 406 that the position of the pointer p is not within the image-area NA but on the left-side outline of the image-area NA, the process returns to Step 402 without shifting the pointer P.

When it is determined that the first and third buttons 18A, 18C are not depressed simultaneously at Step 405, the process goes to Step 408. In Step 408, it is determined whether the second pointer-shift button 18B is depressed. When it is determined that the second pointer-shift button 18B is depressed, the process goes to Step 409, wherein it is determined whether the position of the pointer P is within the image-area NA. When it is determined that the position of the pointer P is within the image-area NA, the process goes to Step 410, wherein the pointer P is shifted downward by one coordinate worth. After Step 410 is performed, the process returns to Step 402. On the other hand, when it is determined that the position of the pointer P is not within the image-area NA but on the lower-side outline of the image-area NA at Step 409, the process returns to Step 402 without shifting the pointer P.

When it is determined that the second button 18B is not depressed at Step 408, the process goes to Step 411. In Step 411, it is determined whether the third pointer-shift button 18C is depressed. When it is determined that the third pointer-shift button 18C is depressed, the process goes to Step 412, wherein it is determined whether the position of the pointer P is within the image-area NA. When it is determined that the position of the pointer P is within the image-area NA, the process goes to Step 413, wherein the pointer P is shifted upward by one coordinate worth. After Step 413 is performed, the process returns to Step 402. On the other hand, when it is determined that the position of the pointer P is not within the image-area NA but on the upper-side outline of the image-area NA at Step 412, the process returns to Step 402 without shifting the pointer P.

When it is determined that the third button 18C is not depressed at Step 411, the process goes to Step 414. In Step 414, it is determined whether the second and third buttons 18B, 18C are depressed simultaneously. When it is determined that the second and third buttons 18B, 18C are depressed simultaneously, the process goes to Step 415, wherein the position of the pointer P and the indicating-pixel $P_c$ is specified, similar to the first embodiment. In Step 416, the pointer P is erased from the monitor 50 to perform the magnifying process. After Step 416 is performed, the interrupt routine is terminated. On the other hand, when it is determined that the second and third buttons 18B, 18C are not depressed simultaneously at Step 414, namely, no button is depressed, the process returns to Step 402. Until the display state is changed to the magnified-display, Steps 402 to 414 are performed repeatedly.

Note that, for the arrangement and the number of push buttons, other arrangements and numbers may be applied.

In the first to third embodiments, the keyboard, touch panel and the pointer shift buttons are used as input devices, however, other input devices, such as a pointing device (mouse) or a joystick, may by applied and further, may be provided at the manipulating section of the video-scope.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No.2000-161773 (filed on May 31, 2000) which is expressly incorporated herein, by reference, in its entirety.

What is claimed is:

1. An electronic endoscope having a video-scope with an image sensor, a video-processor and a display, said video-scope and said display being connected to said video-processor, said electronic endoscope comprising:

an image forming processor that forms a display subject image for display on the basis of an all-pixel subject image, which is formed on said image sensor and composed of substantially all pixels in said image sensor;

a signal processor that generates video signals on the basis of image-pixel signals, which correspond to said display subject image, and outputs said video signals to said display; and a display-state changing processor that changes a display-state from a normal-display to a magnified-display and from the magnified-display to the normal-display, wherein said image forming processor forms a normal-display subject image composed of a smaller number of pixels than that of said all-pixel subject image as said display subject image during the normal-display, an image-resolution of said normal-display subject image being different from that of said all-pixel subject image, and wherein said image forming processor forms a magnified-display subject image composed of pixels arranged within a part-area of said all-pixel subject image as said display subject image during the magnified-display.

2. The electronic endoscope of claim 1, wherein an all pixel number of said image sensor is larger than an effective pixel number, which corresponds to a video standard applied in said electronic endoscope, and said normal-display subject image and said magnified-display subject image are composed of a first pixel number and a second pixel number respectively, both of which are equal to and less than said effective pixel number.

3. The electronic endoscope of claim 2, wherein said image forming processor forms said normal-display subject image by performing a down sampling to said all-pixel subject image.

4. The electronic endoscope of claim 2, further comprising an input device for indicating a given position in a normal-image, which is displayed on said display at the normal-display and corresponds to said normal-display subject image; and an indicating pixel detecting processor that detects an indicated-position selected by said input device and specifies an indicating-pixel corresponding to said indicated-position from the pixels of said all-pixel subject image, wherein said image forming processor forms said magnified-display subject image by defining said indicating-pixel as a center pixel of said part-area and defining said part-area in accordance with the second pixel number.

5. The electronic endoscope of claim 4, wherein said indicating pixel detecting processor determines whether or not said part-area composed of said second pixel number can be defined in said all-pixel subject image on condition that said indicating-pixel becomes the center position of said magnified-display subject image, and wherein said indicating pixel detecting processor changes said indicating-pixel such that said magnified-display subject image composed of said second pixel number is formed, when said part-area can not be defined.

6. The electronic endoscope of claim 4, further comprising an indicator mark displaying processor that generates a character signal corresponding to an indicator mark and superimposes said character signal upon said video signals, such that said indicator mark indicates the given position, wherein said input device comprises a keyboard connected to said video-processor that has a shift key for shifting a position of said indicator mark on said display, said indicator mark displaying processor adjusting the position of said indicator mark in accordance with an operation to said shift key, and wherein said indicating pixel detecting processor detects the position of said indicator mark as the indicated-position and specifies said indicating-pixel from the position of said indicator mark.

7. The electronic endoscope of claim 4, wherein said input device comprises a touch panel connected to said video-processor and arranged on said display, that informs a position touched by an operator to said video-processor, wherein said indicating pixel detecting processor detects the touched position as the indicated-position and specifies said indicating-pixel from said touched position.

8. The electronic endoscope of claim 4, further comprising an indicator mark displaying processor that generates a character signal corresponding to an indicator mark and superimposes said character signal upon said video signals, such that said indicator mark displayed on said display indicates a given position, wherein said input device comprises a manipulating member that shifts the position of said indicator mark and is attached at a manipulating section of said video-scope, said indicator mark displaying processor adjusting the position of said indicator mark in accordance with an operation of said manipulating member, and wherein said indicating pixel detecting processor detects the position of said indicator mark as the indicated-position and specifies said indicating-pixel from the position of said indicator mark.

9. The electronic endoscope of claim 8, wherein said manipulating member has a plurality of push buttons for shifting said indicator mark, said indicator mark displaying processor adjusting the position of said indicator mark in accordance with an operation to said plurality of push buttons.

10. The electronic endoscope of claim 8, wherein said manipulating member is composed of first, second and third push buttons arranged on a tapering end portion of said manipulating section, said first push button arranged on one surface of said tapering end portion and said second and third push buttons arranged on another surface of said tapering end portion, wherein said first, second and third push buttons are arranged such that at least two buttons of said first, second and third push buttons are operated simultaneously by at least two fingers of thumb, index and middle fingers.

11. The electronic endoscope of claim 2, wherein said image forming processor forms said display subject image in said video-scope.

12. The electronic endoscope of claim 11, wherein said image forming processor forms said normal-display subject image by performing a down sampling, said down sampling reading only normal image-pixel signals generated at pixels, by which said normal-display subject image is formed, from said image sensor.

13. The electronic endoscope of claim 11, wherein said image forming processor forms said magnified-display subject image by reading only part image-pixel signals, generated at the pixels arranged within said part-area, from said image sensor.

14. The electronic endoscope of claim 1, further comprising a pixel number determining processor that determines whether or not the pixel number of said image sensor is larger than an effective pixel number, which corresponds to a video standard applied in said electronic endoscope, wherein said image forming processor forms said normal-display subject image and said magnified-display subject image when the pixel number is larger than said effective pixel number.

15. The electronic endoscope of claim 14, wherein said image forming processor forms said all-pixel subject image as said normal-display subject image during the normal-display and forms said magnified-display subject image by performing an interpolation process to said all-pixel subject image during the magnified-display, when the pixel number of said image sensor is not larger than said effective pixel number.

16. An apparatus for displaying normal and magnified images, which is incorporated in an electronic endoscope having a video-scope with an image sensor, a video-processor and a display, said video-scope and said display being connected to said video-processor, said apparatus comprising:

an image forming processor that forms a display subject image for display on the basis of an all-pixel subject image, which is formed on said image sensor and composed of substantially all pixels in said image sensor;

a signal processor that generates video signals on the basis of image-pixel signals corresponding to said display subject image and outputs said video signals to said display; and a display-state changing processor that changes a display-state from a normal-display to a magnified-display and from the magnified-display to the normal-display, wherein said image forming processor forms a normal-display subject image composed of a smaller number of pixels than that of said all-pixel subject image as said display subject image during the normal-display, an image-resolution of said normal-display subject image being different from that of said all-pixel subject image, and wherein said image forming processor forms a magnified-display subject image composed of pixels arranged within a part-area of said all-pixel subject image as said display subject image during the magnified-display.

* * * * *